United States Patent [19]

Bru-Magniez et al.

[11] Patent Number: 5,358,950
[45] Date of Patent: * Oct. 25, 1994

[54] TRIAZOLOPYRIMIDINE DERIVATIVES WHICH ARE ANGIOTENSIN II RECEPTOR ANTAGONISTS

[75] Inventors: Nicole Bru-Magniez, Paris; Eric Nicolai, Caen; Jean-Marie Teulon, La Celle Saint Cloud, all of France

[73] Assignee: Laboratoires UPSA, Agen, France

[*] Notice: The portion of the term of this patent subsequent to Jun. 8, 2010 has been disclaimed.

[21] Appl. No.: 906,526

[22] Filed: Jun. 24, 1992

Related U.S. Application Data

[63] Continuation-in-part of Ser. No. 741,134, Aug. 7, 1991, Pat. No. 5,217,973.

[30] Foreign Application Priority Data

Jul. 5, 1991 [FR] France ............... 91 08486

[51] Int. Cl.⁵ ............... A61K 31/505; C07D 487/04
[52] U.S. Cl. ............... 514/258; 544/263
[58] Field of Search ............... 544/263; 514/258

[56] References Cited

U.S. PATENT DOCUMENTS

| | | | |
|---|---|---|---|
| 4,269,980 | 5/1981 | Hardy et al. | 544/256 |
| 4,883,872 | 11/1989 | Atwal | 544/263 |
| 5,217,973 | 6/1993 | Bru-Magniez et al. | 514/258 |
| 5,223,501 | 6/1993 | Chakravarty et al. | 514/258 |
| 5,231,094 | 7/1993 | Bru-Magniez et al. | 514/233.2 |

FOREIGN PATENT DOCUMENTS

| | | |
|---|---|---|
| 2033121 | 6/1991 | Canada . |
| 0152841 | 8/1985 | European Pat. Off. . |
| 0435827A2 | 7/1991 | European Pat. Off. . |
| WO91/15209 | 10/1991 | PCT Int'l Appl. . |
| 897870 | 5/1962 | United Kingdom . |

Primary Examiner—Emily Bernhardt
Attorney, Agent, or Firm—Rosen, Dainow & Jacobs

[57] ABSTRACT

The present invention relates to the derivatives of formula:

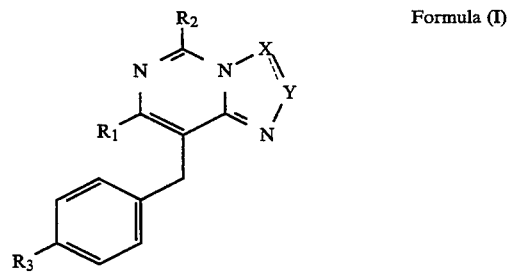

Formula (I)

and to their tautomeric forms as well as to their addition salts and to their use in therapy, in particular for the treatment of cardiovascular diseases, especially for the treatment of hypertension, cardiac insufficiency and diseases of the arterial wall.

9 Claims, No Drawings

TRIAZOLOPYRIMIDINE DERIVATIVES WHICH ARE ANGIOTENSIN II RECEPTOR ANTAGONISTS

This is a continuation-in-part of U.S. patent application No. 07/741,134 filed on Aug. 7, 1991 now U.S. Pat. No. 5,217,973.

The present invention relates to, as new products, the triazolopyrimidine derivatives of general formula (I) below and also to their tautomeric forms and, where appropriate, to their addition salts, especially the pharmaceutically acceptable addition salts.

The compounds in question exhibit a very advantageous pharmacological profile, inasmuch as they are endowed with antagonist properties with respect to angiotensin II receptors. They are hence especially indicated for the treatment of cardiovascular diseases, especially for the treatment of hypertension, for the treatment of cardiac insufficiency and for the treatment of diseases of the arterial wall.

The present invention also relates to the process for preparing the said products and to their uses in therapy.

These triazolopyrimidine derivatives and their tautomeric forms are characterised in that they correspond to the general formula (I)

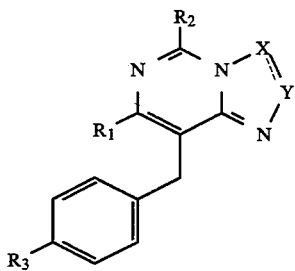

Formula (I)

In the formula (I), $R_1$ represents a lower alkyl radical having 1 to 6 carbon atoms or a $C_3$–$C_7$ cycloalkyl radical, $R_2$ represents a hydrogen atom, a lower alkyl radical having 1 to 6 carbon atoms, a lower haloalkyl radical having 1 to 6 carbon atoms, a group $NR_4R'_4$, an NH—$NH_2$ group or a group $(CH_2)_m$—$OR_4$ or —$(CH_2)_m$—$SR_4$; $R_4$ and $R'_4$, which may be identical or different, represent a hydrogen atom or a lower alkyl radical having 1 to 6 carbon atoms and m represents an integer from 0 to 5, the assembly —X··Y— or —Y  X— represents one of the following bivalent radicals:

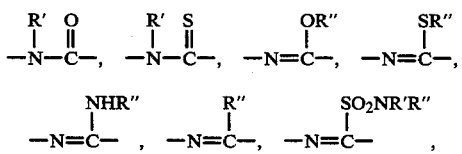

in which R' and R", which may be identical or different, represent:
a hydrogen atom, a lower alkyl radical having 1 to 6 carbon atoms or a lower haloalkyl radical having 1 to 6 carbon atoms,
a group $(CH_2)_nCOOR_5$, $(CH_2)_{n'}$—O—$R_5$, $(CH_2)_{n'}$—O—CO—$R_5$ or $(CH_2)_{n'}$—S—$R_5$, n being an integer from 0 to 5, n' being an integer from 1 to 5 and $R_5$ being a hydrogen atom or a lower alkyl radical having 1 to 6 carbon atoms,
a phenyl, pyridyl, thienyl or furyl radical,
$R_3$ represents an $NO_2$ or $NH_2$ group or represents one of the following radicals:

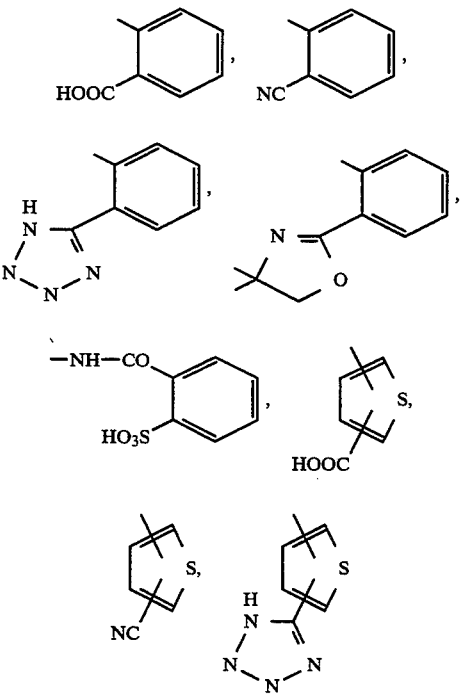

The abovementioned derivatives must also be considered in their tautomeric forms and may take the form of addition salts, especially of pharmaceutically acceptable addition salts.

In the description and the claims, lower alkyl is understood to mean a linear or branched hydrocarbon chain having from 1 to 6 carbon atoms. A lower alkyl radical is, for example, a methyl, ethyl, propyl, isopropyl, butyl, isobutyl, tert-butyl, pentyl, isopentyl, hexyl or isohexyl radical.

Lower haloalkyl radical is understood to mean an alkyl radical having 1 to 6 carbon atoms, 1 to 7 hydrogen atoms of which have been substituted by 1 to 7 halogen atoms. A lower haloalkyl radical is, for example, a trifluoromethyl radical, a 2,2,2-trifluoroethyl radical, a pentafluoroethyl radical, a 2,2-difluoro-3,3,3-trifluoropropyl radical, a heptafluoropropyl radical, or a chloromethyl or bromomethyl radical.

$C_3$–$C_7$ cycloalkyl radical is understood to mean a saturated cyclic hydrocarbon radical; such a radical is preferably a cyclopropyl, cyclobutyl, cyclopentyl, cyclohexyl or cycloheptyl radical.

Halogen is understood to mean a chlorine, bromine, iodine or fluorine atom.

The invention relates especially to the derivatives of general formula (I) in which:

$R_1$ represents a lower alkyl radical having 1 to 6 carbon atoms or a $C_3$–$C_7$ cycloalkyl radical:

$R_2$ represents a hydrogen atom, a lower alkyl radical having 1 to 6 carbon atoms, an NH-$NH_2$ group or a group $(CH_2)_mOR_4$ or $(CH_2)_mSR_4$; $R_4$ representing a hydrogen atom or a lower alkyl radical having 1 to 6 carbon atoms and m representing an integer from 0 to 2;

the assembly —X···Y— represents a radical selected from the following bivalent radicals:

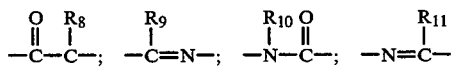

in which:

$R_8$ represents a radical selected from the group consisting of a hydrogen atom, —(CH$_2$)$_n$OH, —(CH$_2$)$_n$COOH, —R$_{12}$ or —(CH$_2$)$_n$COOR$_{12}$; R$_{12}$ representing a lower alkyl radical having 1 to 6 carbon atoms and n an integer equal to 1 or 2;

$R_9$ represents a hydrogen atom or an —SH radical;

$R_{10}$ represents a hydrogen atom or a lower alkyl radical having 1 to 6 carbon atoms;

$R_{11}$ represents a radical selected from the group consisting of a hydrogen atom, a lower alkyl radical having 1 to 6 carbon atoms, a lower haloalkyl radical having 1 to 6 carbon atoms, phenyl, pyridyl, —O(CH$_2$)$_n$OH, —OR$_{12}$, —O(CH$_2$)$_n$OCOR$_{12}$, SH, —SR$_{12}$, —S(CH$_2$)$_n$COOR$_{12}$, —S(CH$_2$)$_n$OCOR$_{12}$, —NH(CH$_2$)$_n$COOR$_{12}$, —NR$_{13}$R$_{14}$, SO$_2$NR$_{13}$R$_{14}$, (CH$_2$)$_n$OH, (CH$_2$)$_n$OR$_{12}$, COOH, COOR$_{12}$, (CH$_2$)$_n$COOH, or (CH$_2$)$_n$COOR$_{12}$; n and R$_{12}$ being defined as stated above, R$_{13}$ and R$_{14}$, which may be identical or different, representing a hydrogen atom or a lower alkyl radical having from 1 to 6 carbon atoms;

$R_3$ represents one of the following radicals:

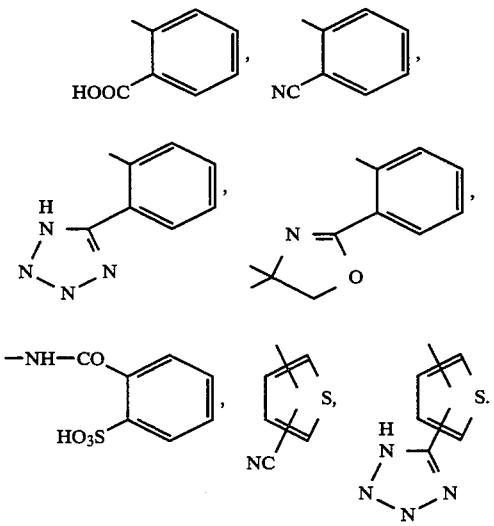

According to a variant of embodiment, R$_1$ is an n-propyl group;

according to another variant of embodiment, R$_1$ is an n-butyl group;

according to another variant of embodiment, R$_1$ is an ethyl group;

according to a variant of embodiment, R$_2$ is a methyl group;

according to another variant of embodiment, R$_2$ is an ethyl group;

according to another variant of embodiment, R$_2$ is a methoxymethyl group;

according to a variant of embodiment, the assembly —X Y— represents one of the following bivalent radicals

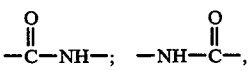

or their tautomeric form;

according to another variant of embodiment, the assembly —X···Y— represents the radical

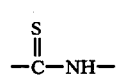

or its tautomeric-form;

according to another variant of embodiment, the assembly —X···Y— represents the radical

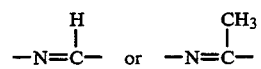

according to another variant of embodiment, the assembly —X···Y— represents the radical

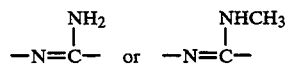

or their tautomeric form;

according to another variant of embodiment, the assembly —X···Y— represents the radical

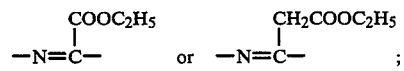

according to a variant of embodiment, R$_3$ is a 2-(5-tetrazolyl)phenyl group.

Especially preferred compounds of the invention are those which are selected from the products of formula:

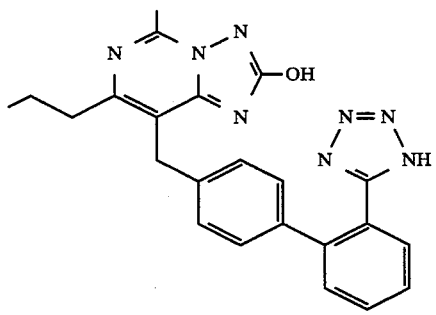

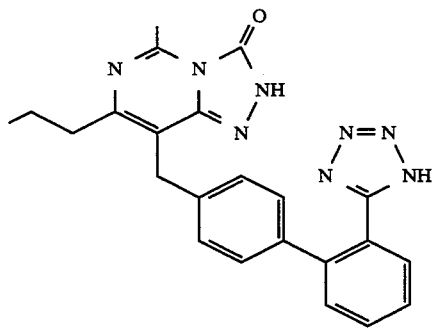

-continued

-continued

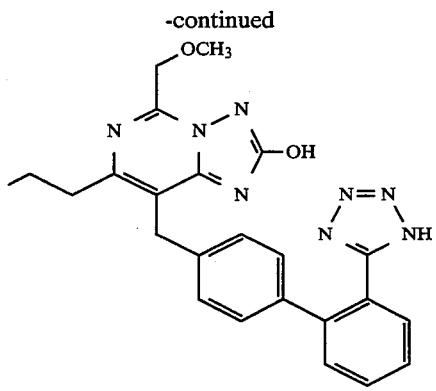

According to the invention, the compounds of formula (I) may be synthesised according to the following reaction sequence:

The alkyl 3-oxoalkanoates of formula (II):

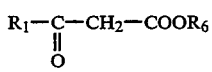

Formula (II)

in which $R_1$ is defined as above and $R_6$ represents a lower alkyl radical, preferably methyl or ethyl, will be prepared by methods known per se, such as for example, the Claisen reaction or the method employing Meldrum's acid, it being possible to find these methods in the following literature references:

OIKAWA, Y. SUGANO, K. and YONEMITSU, O.; J. Org. Chem., 1978 43 (10), 2087–88.

WIERENGA, W. and SKULNICK, H. I.; J. Org. Chem., 1979, 44(2), 310–1.

HOUGHTON, R. P. and LAPHAM, D. J.; Synthesis, 1982, 6, 451–2.

BRAM, G. and VILKAS, M.; Bull. Soc. Chim. France, 1964, (5), 945–51.

By benzylation of the compounds of formula (II) with compounds of formula (III)

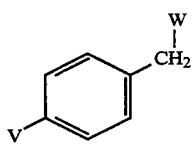

Formula (III)

in the presence of a base such as a sodium or potassium carbonate in acetone, a sodium or potassium alcoholate in an alcohol, a sodium or lithium hydride in solvents such as tetrahydrofuran, dioxane or dimethylformamide, for example at a temperature of between 50° and 100° C., or alternatively in the presence of one equivalent of lithium chloride or bromide and two equivalents of diisopropylethylamine under reflux of tetrahydrofuran according to the reference: SUNG-EUN YOO and KYU YANG YI; Bull. Korean. Chem. soc., 1989, 1.0 (1), 112, the compounds of formula:

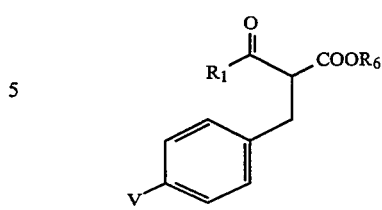

Formula (IV)

will be obtained.

In the formula (IV), $R_1$ and $R_6$ are defined as above and V has the see definition as in the formula These compounds of formula (IV) may also be obtained by condensation of an aldehyde of formula (III).

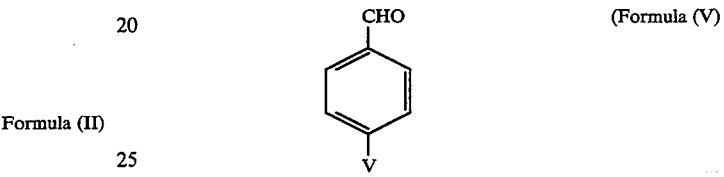

(Formula V)

with the compounds of formula (II), followed by a hydrogenation in the presence of a catalyst such as Raney nickel, palladium on charcoal or platinum oxide in a solvent such as an alcohol or tetrahydrofuran under pressure or at atmospheric pressure when the substitutions present permit it.

More generally, methods of preparation of the compounds of formula (IV) will be found in the following references:

DURGESHWARI, P. and CHAUDHURY, N. D.; J. Ind. Chem. Soc., 1962, 39, 735–6

ZAUGG, H. E., DUNNIGAN, D. A., MICHAELS, R. J. and SWETT, L. R.; J. Org. Chem., 1961, 26, 644–51

BORRIES KUBEL; Liebigs. Ann. Chem. 1980, 1392–1401

IOFFE, T., POPOV, E. M., VATSURO, K. V., TULIKOVA, E. K. and KABACHNIK, M. I.; Tetrahedron, 1962, 18, 923–940

SHEPHERD, T. M.; Chem. Ind. (London), 1970, 17, 657.

In the formula (III), W represents a halogen atom, preferably chlorine or bromine.

In the same formula:

V can be a nitro group; the derivative of formula (III) is then a commercial product;

V can be a group

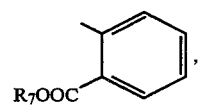

$R_7$ being a lower alkyl or a benzyl radical; the compounds of formula (III) are then prepared by reaction of a magnesium derivative of p-bromotoluene with a compound of formula

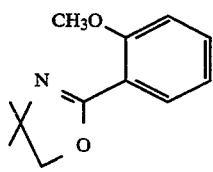

to obtain a compound of formula:

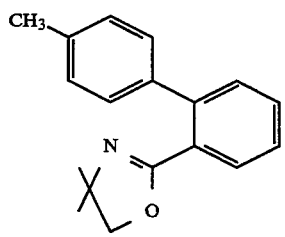

which is then hydrolysed to yield the compound of formula:

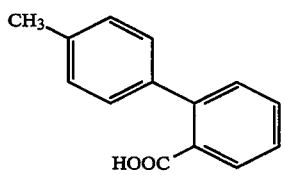

Procedures for the three steps described above will be found in the reference:

MEYERS, A. I. and MIHELICH, E. D.; J. Am. Chem. Soc., 1975, 97, 7383.

The acid is then esterified with an alcohol of formula $R_7OH$, $R_7$ being defined as above.

These derivatives are then brominated or chlorinated, for example with N-bromosuccinimide, N-chlorosuccinimide or bromine in a solvent such as carbon tetrachloride or dibromoethane or dichloroethane, to yield the compounds of formula (III) in which V is the group

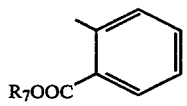

V can be the group

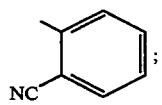

in this case, the compound:

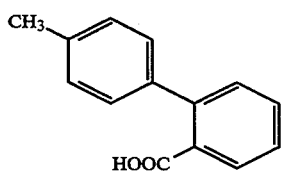

prepared above will be converted to the primary amide by the action of the acid chloride, obtained with thionyl chloride or phosphorus oxychloride, on ammonia solution, and this amide will be converted to the nitrile by the action of phosphorus oxychloride in dimethylformamide or thionyl chloride. The nitrile obtained:

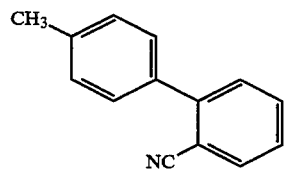

will then be brominated or chlorinated under the same conditions as the above ester to yield the compounds of formula (III) in which V is the group

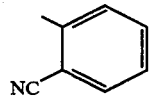

Another variant of preparation consists in treating the derivative

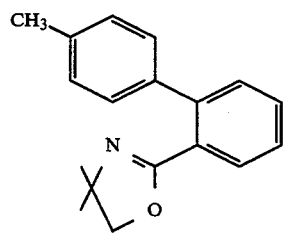

prepared above, with phosphorus oxychloride in the presence of pyridine to yield the compound

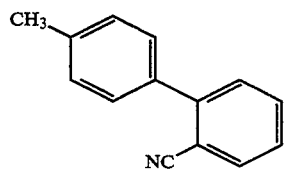

Another variant of embodiment consists in preparing the magnesium derivative of p-(methoxymethyl)bromobenzene:

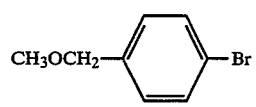

which will then be reacted with the derivative of formula

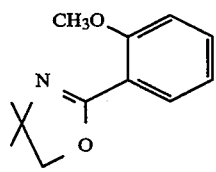

to yield the derivative of formula

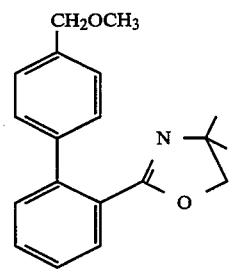

which, on demethylation with, for example, a BBr₃ treatment, will yield the compound of formula

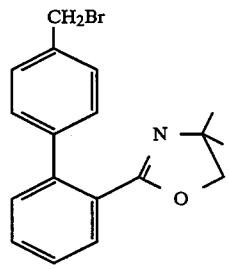

which, by condensation according to the conditions described above with the derivatives of formula (II), will yield the compounds of formula (IV) in which V represents a group

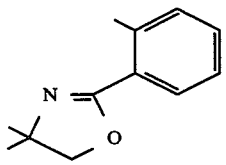

This compound may optionally be treated with phosphorus oxychloride in the presence of pyridine to yield the compounds of formula (IV) in which V represents

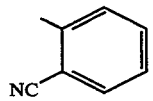

V can be a group

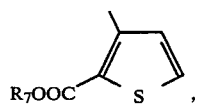

R₇ being a lower alkyl or benzyl radical; the corresponding compounds of formula (III) are obtained in the following manner:

from 3-(p-methylphenyl)-2-thiophenecarboxylic acid

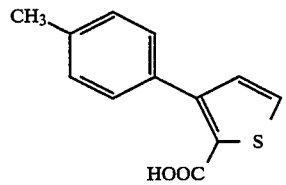

the preparation of which may be found in the reference:
FISSELMANN, H and PLABITCH, H; Ger. Offen.: 1,092,929 (1960); CA: 57: 5894 g, the compounds of formula:

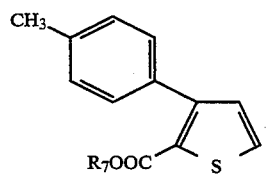

will be obtained by esterification using an alcohol of formula R₇OH, R₇ being defined as above, by conventional methods known to those skilled in the art.

These compounds are then treated with N-chlorosuccinimide or N-bromosuccinimide in a solvent such as carbon tetrachloride or dibromoethane, for example, to give the compounds of formula (III) in which V represents the group

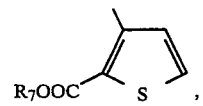

R₇ being defined as above
V can be the group

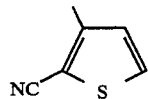

in this case the corresponding compounds of formula (III) will be prepared in the following manner:

from the compound 3-(p-methylphenyl)-2-thiophenecarboxylic acid, the preparation of which is given above, by treatment with thionyl chloride and then ammonia, the amide compound is obtained, which compound is then dehydrated with thionyl chloride or phosphorus oxy-chloride without solvent or in dimethylformamide to yield the nitrile compound:

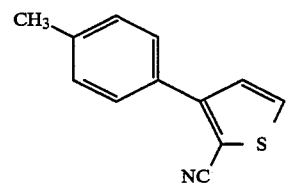

This nitrile compound is then halogenated with N-chlorosuccinimide or N-bromosuccinimide in a solvent such as carbon tetrachloride or dibromoethane to give the compounds of formula (III) in which V represents the group

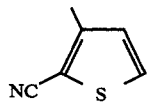

V can be a group

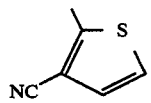

in this case the corresponding compounds of formula (III) are synthesised in the following manner:

from 4-chloro-4'-methylbutyrophenone of formula:

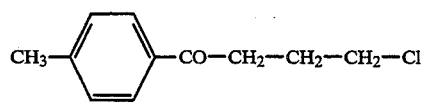

the preparation of which may be found in Patent BE: 577,977 of 15th May 1959, CA:54., 4629 c, by treatment with phosphorus oxychloride and dimethylformamide according to the conditions described in the reference:

VOLODINA. M. A., TENENT'EV. A. P., KUDRYASHOVA. V. A., and KABOSHINA. L. N., Khim. Geterosikl. Soedim, 1967, 5–8, the compound of formula:

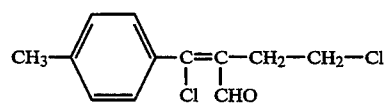

will be obtained.

This compound is then treated with sodium sulphide in a solvent such as tetrahydrofuran under reflux to give the derivative:

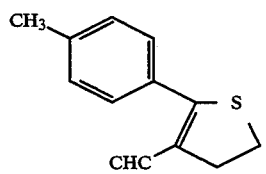

which is then converted in two steps to the nitrile derivative by dehydration of the oxime formed from the aldehyde and hydroxylamine. This dehydration may be performed, for example, using acetic anhydride, to give the nitrile compound:

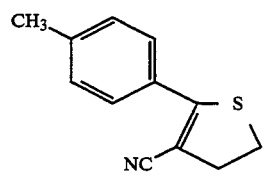

which may then be aromatised by treatment with bromine in carbon tetrachloride and then with potassium tertbutylate in tetrahydrofuran to give the compound:

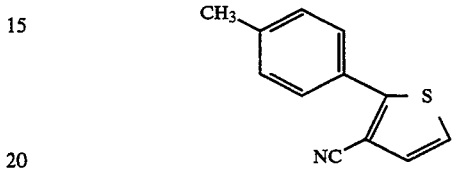

This compound may then be chlorinated or brominated with halogenating agents such as N-chlorosuccinimide or N-bromosuccinimide in a solvent such as carbon tetrachloride or dibromoethane to give the compounds of formula (III) in which V represents the group

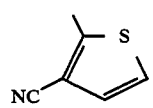

V can be a group

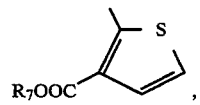

$R_7$ being defined as above; in this case, the corresponding compounds of formula (III) may be prepared from the nitrile prepared above, of formula:

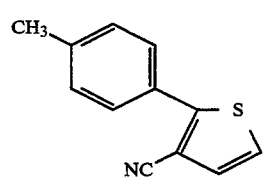

by conventional hydrolysis of the nitrile function and then esterification of the acid obtained, or by proceeding directly from the nitrile function to the ester function according to methods known to those skilled in the art, followed by a chlorination or bromination of the ester with N-chlorosuccinimide or N-bromosuccinimide in carbon tetrachloride or dibromoethane, for example.

In the formula (V), V has the same definition as in the formula (III), but the condensation method employing the aldehydes of formula (V) and the keto esters of formula (II) will be used only when V possesses a function which is not incompatible with hydrogenation.

These compounds of formula (V) may be prepared from the derivatives of formula (III) by methods known to those skilled in the art, such as as the Sommelet reaction, an example of which may be found in the reference: Organic Synthesis Collec. Vol. IV p.918 or the nitropropane method described in the reference: Organic Synthesis Collec. Vol. IV p.932.

By the action of a compound of formula (VI)

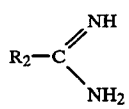

Formula (VI)

in which $R_2$ is defined as above, on the compounds of formula (IV), there will be obtained, by condensation in an alcohol in the presence of a sodium or potassium alcoholate at a temperature which can range from room temperature to the boiling point of the solvent, the compounds of formula (VII) or their tautomeric form

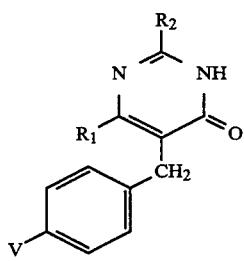

Formula (VII)

in which $R_1$, $R_2$ and V are defined as above.

The compounds of formula (VI) are commercial, or will be prepared according to methods known to those skilled in the art, by the action of ammonia in an alcoholic medium on the imino ethers or their hydrochloride of formula $R_2C(OR)=NH$, which are themselves prepared from the corresponding nitrile of formula $R_2CN$ by treatment with hydrogen chloride gas in the corresponding alcohol.

By heating in $POCl_3$, for example, the derivatives of formula (VII), the derivatives of formula (VIII):

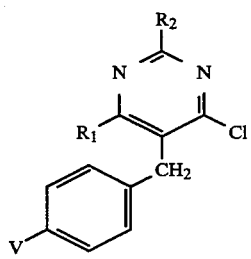

Formula (VIII)

in which $R_1$, $R_2$ and V are defined as above, will be obtained.

Heating the derivatives of formula (VIII) in the presence of hydrazine or hydrazine hydrate in an alcohol under reflux will enable the derivatives of formula (IX):

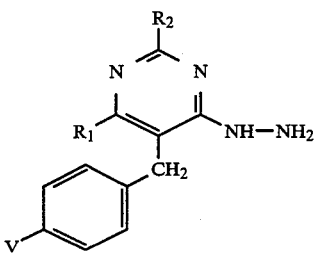

Formula (IX)

in which $R_1$, $R_2$ and V are defined as above, to be obtained.

These derivatives of formula (IX) will be cyclised by the action of carbonyldiimidazole under reflux of tetrahydrofuran, or by the action of urea by heating without a solvent or in a solvent such as N-methylpyrrolidone, or by the action of methyl or ethyl chloroformate, or by the action of phosgene or a phosgene precursor in a solvent such as toluene, or by the action of potassium xanthogenate under reflux of an alcohol such as methoxyethanol, for example, or by the action of carbon disulphide in an alcohol, for example ethanol, in the presence or absence of an amine such as tri-ethylamine, to yield the compounds of formula (X):

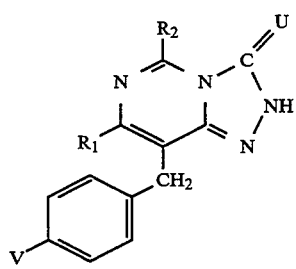

Formula (X)

in which $R_1$, $R_2$ and V are defined as above and U represents an oxygen or sulphur atom.

The derivatives of formula (X) in which U is an oxygen atom may also be obtained directly by heating the derivatives of formula (VIII) with ethyl carbazate or methyl carbazate.

These triazolo[4,3-c]pyrimidine derivatives of formula (X) may undergo an isomerisation in a basic medium in water or in a water/alcohol mixture at a temperature of between 20° and 100° C., and optimally in the region of 60° C., it also being possible to carry out this isomerisation in an acid medium by heating in dichlorobenzene in the presence of formic acid or in acetic acid in the presence or absence of sodium acetate or potassium acetate, to yield the triazolo[1,5-c]pyrimidine compounds of formula (XI):

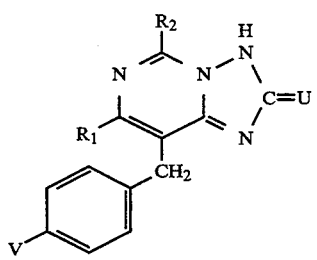

Formula (XI)

in which $R_1$, $R_2$, V and U are defined as above.

The compounds of formula (XI) in which U is a sulphur atom may also be obtained directly, by heating the derivatives of formula (IX) and carbon disulphide in pyridine or butanol under reflux.

The derivatives of formula (X) or of formula (XI) may be metalated. Depending on the conditions of metalation and the nature of the compound, the substitution will be directed towards the nitrogen atom or towards the hetero atom U. In particular, when U represents a sulphur atom, substitution will take place mainly on the S; when U represents an oxygen atom, the compounds of formula (X) will mainly yield the N-substituted derivatives, and the compounds of formula (XI) will mainly yield the O-substituted compounds. To favour N-substitution, it will be preferable to use as a metalating agent sodium hydride, lithium hydride or a sodium or potassium alcoholate in a solvent such as dimethylformamide, tetrahydrofuran or an alcohol; to favour O-substitution, sodium hydroxide, potassium hydroxide or a sodium or potassium carbonate in a solvent such as acetone or methyl ethyl ketone will be preferred as a metalating agent.

By reacting these metalated derivatives with halogenated derivatives of formula:

A—(CH$_2$)$_n$—CH$_3$
A—(CH$_2$)$_n$—COOR$_5$
A—(CH$_2$)$_{n'}$—O—R$_5$
A—(CH$_2$)$_{n'}$—OCOR$_5$
A—(CH$_2$)$_{n'}$—S—R$_5$ in which formulae A is a halogen atom, more especially chlorine or bromine, and n, n' and R$_5$ have the same meaning as above, the derivatives substituted on the triazole ring (either on a nitrogen or via the oxygen or sulphur atom) with the groups:

—(CH$_2$)$_n$—CH$_3$
—(CH$_2$)$_n$—COOR$_5$
—(CH$_2$)$_{n'}$—OR$_5$
—(CH$_2$)$_{n'}$—OCOR$_5$
—(CH$_2$)$_{n'}$—S—R$_5$ will be obtained (however, to carry out these reactions, the derivatives in which R$_5$ is a lower alkyl having 1 to 6 carbon atoms may, in some cases, be the preferred choice; the derivatives in which R$_5$ represents a hydrogen atom will be obtained by hydrolysis).

The derivatives of formula (X') or their tautomeric form

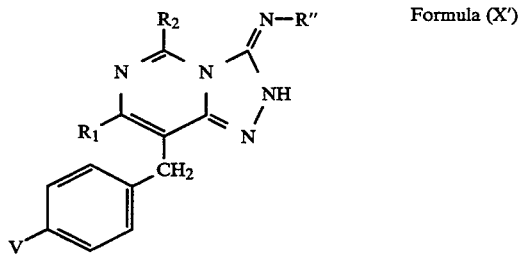

Formula (X')

in which R$_1$, R$_2$, R" and V are defined as above, may be prepared in the following manner:

in the case where R" is a hydrogen atom, by the action of cyanogen bromide on the derivatives of formula (IX);

in the case where R" is other than a hydrogen atom, in several steps:

either by the action, on the derivatives of formula (IX), of an isocyanate of formula O=C=N—R", where R" is defined as above but other than a hydrogen atom, followed by a cyclisation of the urea obtained by heating with POCl$_3$, for example, or by the action, on the derivatives of formula (IX), of an isothiocyanate of formula S=C=N—R", where R" is defined as above but other than a hydrogen atom, followed by methylation of the thiourea obtained to S—CH$_3$ with methyl iodide and then thermal cyclisation of this thiourea derivative by heating in a suitable solvent which can be, for example, an alcohol.

The derivatives of formula (XI') or their tautomeric form:

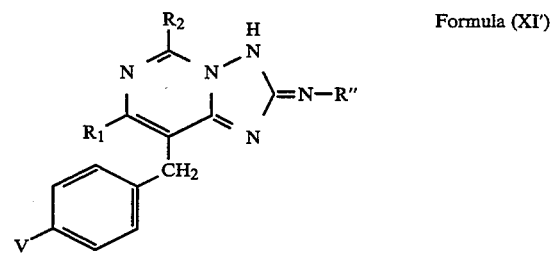

Formula (XI')

in which R$_1$, R$_2$, R" and V are defined as above, may be obtained by isomerisation of the compounds of formula (X') according to the isomerisation conditions described above.

The derivatives of formula (X"):

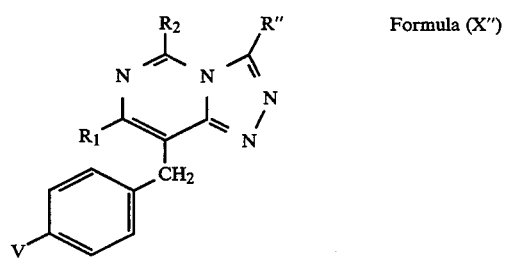

Formula (X")

in which R$_1$, R$_2$, R" and V are defined as above, may be prepared in two different ways:

either by cyclisation, by heating with an ortho ester of formula R"—C(OMe)$_3$ or R"—C(OEt)$_3$, R" being defined as above, of the hydrazinopyrimidine of formula (IX), or by cyclisation, using POCl$_3$, of the hydrazide obtained by the action of an acid chloride of formula R"COCl or of the corresponding methyl or ethyl ester, R" being defined as above, on the hydrazinopyrimidine of formula (IX).

Isomerisation of the derivatives of formula (X"), performed by heating in formic acid or acetic acid, will enable the triazolo [1,5-c]pyrimidine compounds of formula (XI"):

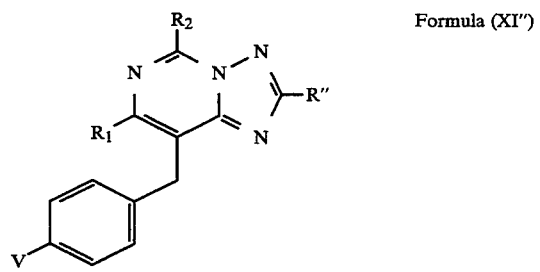

Formula (XI")

in which $R_1$, $R_2$, $R''$ and $V$ are defined as above, to be obtained.

More generally, some methods of preparation of triazolopyrimidines described in the following references may be used:

MILLER, G. W. and ROSE, F. L.; J. Chem. Soc., 1963, 5642–5659

MILLER, G. W. and ROSE, F. L.; J. Chem. Soc., 1965, 3357–3368

MILLER, G. W. and ROSE, F. L.; J. Chem. Soc., 1965, 3369–3372

BROWN, D. J. and NAGAMATSU, T.; Aust. J. Chem. 1978(31), 2502–2515

BROWN, D. J., GRIGG, G. W., IWAI, Y., MAC ANDREW, K. N., NAGAMATSU, T. and VAN HEESWYCK, R.; Aust. J. Chem. 1979(32), 2713–2726

MILLER, G. W. and ROSE, F. L.; Patent GB 951,652 of 11th Mar. 1964

MILLER, G. W. and ROSE, F. L.; Patent GB 859,287 of 18th Jan. 1961.

Treatment with sodium chloride of the derivatives of formula (XI) in which U represents a sulphur atom, in concentrated hydrochloric acid in the cold state, will enable the derivatives of formula:

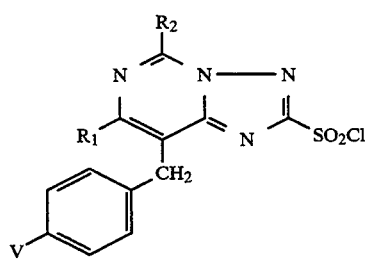

in which $R_1$, $R_2$ and $V$ are defined as above, to be obtained, which derivatives will be reacted with amines of formula $HNR'R''$, in which $R'$ and $R''$ are defined as above, to yield the derivatives of formula (XI'''):

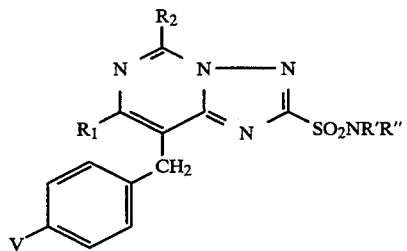

Formula (XI''')

in which $R_1$, $R_2R'$, $R''$ and $V$ are defined as above.

The derivatives of formula (X), (XI), (X'), (XI'), (X''), and (XI''') may be collectively grouped together with the derivatives substituted on a nitrogen of the triazole or substituted on the triazole via an oxygen or sulphur atom in the formula (XII):

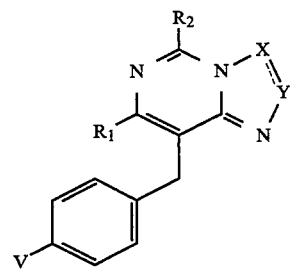

Formula (XII)

in which $R_1$, $R_2$, X, Y and V are defined as above.

Another variant of embodiment, in the case where $R_2$ represents $NH-NH_2$ or $NR_4R'_4$, will consist in treating with hydrazine hydrate or an amine $HNR_4R'_4$ the compound of formula (XII) in which $R_2$ represents an $SCH_3$ group, this compound itself being obtained as described above, using S-methylthiourea or thiourea as a compound of formula (VI), the derivative in which $R_2=SH$ obtained then being methylated with methyl iodide according to conditions known to those skilled in the art.

The compounds of formula (XII) in which:

V is a nitro group may undergo a catalytic hydrogenation, for example in the presence of Raney nickel, in an alcohol at atmospheric pressure or under pressure, to yield the compound of formula (XII) in which V is an amino group.

By the action of sulphobenzoic anhydride on these amino compounds, the compounds of general formula (I) in which $R_3$ represents the group

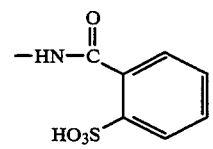

will be obtained.

The compounds of formula (XII) in which:
V is the group

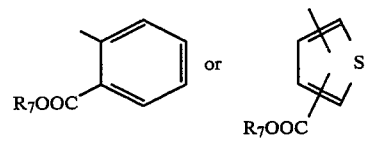

will be hydrolysed, or hydrogenated in the presence of a catalyst such as palladium in the case where $R_7$ is a benzyl, to yield the compounds of formula (T) in which $R_3$ is a group

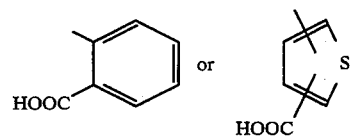

The compounds of formula (XII) in which:
V is the group

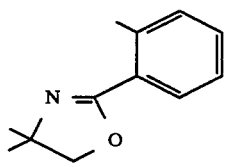

may be converted to a compound of formula (XII) in which V is the group

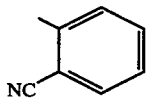

by the action of POCl₃ in the presence of pyridine, for example.

The compounds of formula (XII) in which:
V is a group

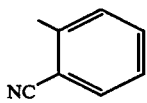

may react with one equivalent of sodium azide in a solvent such as dimethylformamide in the presence of an ammonium salt such as ammonium chloride, or by heating in toluene with trimethyltin azide followed by a treatment with gaseous hydrochloric acid in tetrahydrofuran, to yield the compounds of general formula (I) in which $R_3$ represents a group

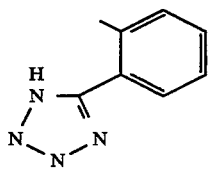

To carry out this reaction, in the case where $R_2$, X or Y possess an aliphatic alcohol function, it can be desirable to protect the latter according to methods known to those skilled in the art by an acetate or a tetrahydropyran, and then to liberate it, if necessary, after formation of the tetrazole.

The compounds of formula (XII) in which:
V represents the group

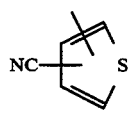

may be treated with a trialkyltin azide in toluene under reflux and then with gaseous hydrochloric acid in tetrahydrofuran to yield the derivatives of formula (I) in which $R_3$ represents the group

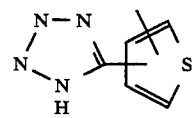

To carry out this reaction, in the case where $R_2$, X or Y possess an aliphatic alcohol function, it can be desirable to protect the latter according to methods known to those skilled in the art by an acetate or tetrahydropyran, and then to liberate it, if necessary, after formation of the tetrazole.

Other alternatives for preparation of the compounds of formula (I) may also be used.

In particular, the hydroxypyrimidines of formula (XIII)

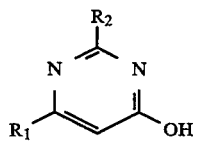

Formula (XIII)

in which $R_1$ and $R_2$ are defined as above, may be prepared by the action of the keto esters of formula (II) on the derivatives of formula (VI) according to the methods described above.

These pyrimidines will be brominated by the action of bromine in acetic acid to yield the compounds of formula (XIV)

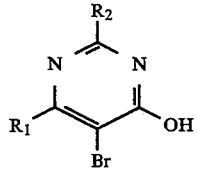

Formula (XIV)

in which $R_1$ and $R_2$ are defined as above.

The compounds of formula (XIV) will then be converted, as described above, to the chlorinated compounds of formula (XV) by the action of POCl₃

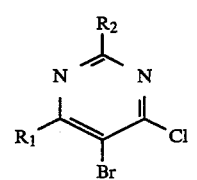

Formula (XV)

in which $R_1$ and $R_2$ are defined as above.

The derivatives of formula (XV) will undergo the same conversions as the derivatives of formula (VIII) to yield the derivatives of formula (XVI)

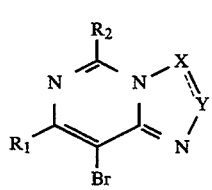

Formula (XVI)

in which $R_1$, $R_2$, X and Y are defined as above.

Another method of synthesis of the derivatives of formula (XVI) will consist in brominating, by the action of bromine in acetic acid, the derivatives of formula (XVII)

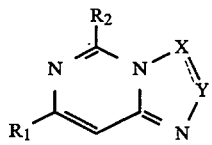

Formula (XVII)

in which R₁, R₂, X and Y are defined as above, the derivatives of formula (XVII) being prepared according to the same synthesis scheme but from the derivatives of formula (XIII).

The action, for example, of the derivative:

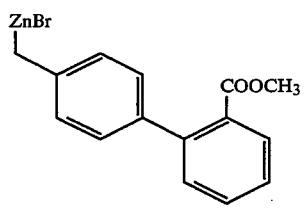

prepared from the derivative of formula (III) in which V is the group

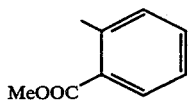

and W a bromine atom, with activated zinc powder in tetrahydrofuran on the derivative of formula (XVI) in the presence of Pd(PPh₃)₄ under reflux of tetrahydrofuran will enable the derivatives of formula (I) in which R₃ represents the group

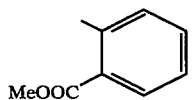

to be obtained.

The ester function COOMe may be converted to acid, amide, nitrile and tetrazole according to the reaction sequences described above. More generally speaking, the use of the derivative

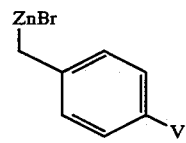

V having the same meaning as above and prepared in the same manner, will enable the derivatives of formula (I) to be obtained.

Another method of access to the derivatives of formula (I) will consist in treating the derivative of formula (XIII), in which, for example, R₂=CH₃ according to the sequence of reactions described above:

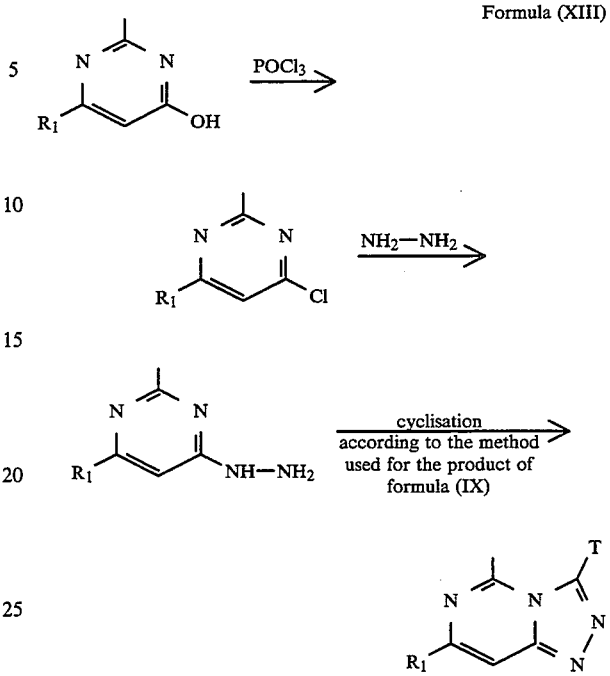

hydrolysis in an acid medium of the 1,2,4-triazolo[4,3-c]-pyrimidine, in which R₁ has the same meaning as above and where T is R″ defined above but also represents an OH or SH group, will yield the compounds of formula (XVIII)

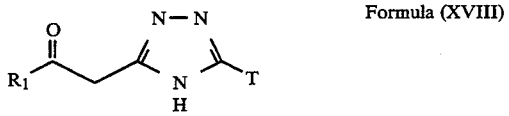

Formula (XVIII)

in which R₁ and T have the same meaning as above.

These derivatives of formula (XVIII) may be condensed with an aldehyde of formula (V) to yield the compounds of formula (XIX)

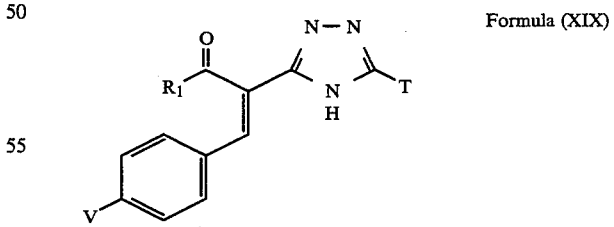

Formula (XIX)

in which R₁, T and V are defined as above.

These derivatives of formula (XIX) will be cyclised by the action of an aldehyde of formula R₂CHO, R₂ being defined as above, in the presence of ammonia, to yield the compounds of formula (I), or will undergo a reduction using sodium cyanoborohydride, for example, to yield the compounds of formula (XX)

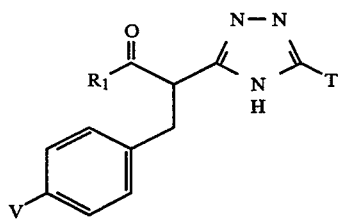

Formula (XX)

in the formula (XX), R₁, V and T are defined as above.

These derivatives of formula (XX) will then be cyclised by the action of a derivative of formula (VI) or by the action of an imino ether of formula R₂C(OR)=NH to yield the compounds of formula (I).

Another method of access to the derivatives of formula (I) will consist in preparing, according to the scheme established above, the compounds of formula (XII) already mentioned but in which V represents an aldehyde or an aldehyde precursor. In this case the keto ester of formula (II) will be substituted according to the methods described above with a derivative of formula

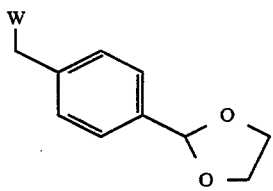

in which W is a halogen, preferably bromine or chlorine, atom.

This method will enable the derivatives of formula (XXI) to be obtained after hydrolysis of the acetal in an acid medium

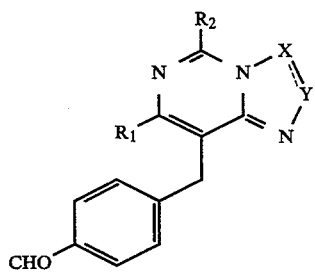

Formula (XXI)

in which R₁, R₂, X and Y are defined as above; these aldehydes will be condensed with malonitrile to yield the compounds of formula (XXII)

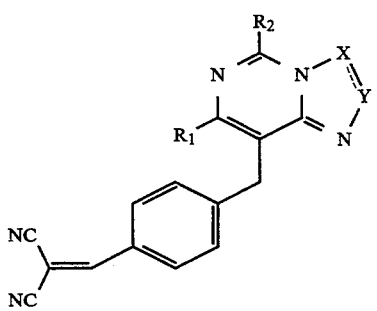

Formula (XXII)

in which R₁, R₂, X and Y are defined as above, which will themselves be condensed in toluene, for example, with 1,3-butadien-4-ylmorpholine, obtained by condensation of crotonaldehyde with morpholine, according to the reference:

Bir SAIN and Jagir S.SANDHU; J. Org. Chem. 1990, 55, 2545, to yield the compounds of formula (XII) in which v represents the group

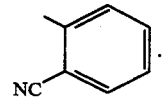

Conversion of the nitrile to the acid function may be carried out by acid or basic hydrolysis; conversion of the nitrile function to the tetrazole function will be done by the methods described above.

Addition salts of some compounds of formula (I) may be obtained, especially pharmaceutically acceptable addition salts. There may be mentioned, in particular, when R₂, R₃ or R" or R" possess an acid function, the sodium, potassium and calcium salts, the salts of an amine such as dicyclohexylamine or those of an amino acid such as lysine; and when R₂, R₃, R' or R" possess an amine function, the salts of inorganic or organic acids, such as hydrochloride, methanesulphonate, acetate, maleate, succinate, fumarate, sulphate, lactate or citrate.

The new compounds according to the invention possess noteworthy pharmacological properties as angiotensin II receptor antagonists, and may be used in therapy for the treatment of cardiovascular diseases, especially for treating hypertension, cardiac insufficiency and diseases of the arterial wall.

Thus, the invention encompasses pharmaceutical compositions containing as active principle the medicinal products consisting of a pharmaceutically effective amount of at least one compound of formula (I), as defined above, as well as, where appropriate, its pharmaceutically acceptable addition salts.

These compositions may be administered buccally, rectally, parenterally, transdermally or via the eye.

These compositions can be solid or liquid, and be presented in the pharmaceutical dosage forths commonly used in human medicine, such as, for example, simple or sugar-coated tablets, hard gelatin capsules, granules, suppositories, injections, transdermal systems and eye washes. They are prepared according to the methods commonly employed. The active principle, consisting of a pharmaceutically effective amount of at least one compound of the formula (I) defined as above or one of its pharmaceutically acceptable addition salts, may be incorporated therein with excipients customarily employed in these pharmaceutical compositions, such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colourings.

The invention also covers a pharmaceutical composition having angiotensin II receptor antagonist activity, permitting, in particular, a favourable treatment of cardiovascular diseases, especially hypertension, cardiac insufficiency and diseases of the arterial wall, characterised in that it comprises a pharmaceutically effective amount of at least one compound of formula (I), mentioned above, or one of its pharmaceutically acceptable addition salts, which can be incorporated in a pharmaceutically acceptable excipient, vehicle or carrier.

The dosage varies, in particular, in accordance with the administration route, the condition being treated and the subject in question.

For example, in an adult of average weight of 60 to 70 kg, it can vary between 1 and 400 mg of active principle in one or several daily doses taken orally, or from 0.01 to 50 mg in one or several daily doses administered parenterally.

The invention also covers a process for preparing a pharmaceutical composition, characterised in that a pharmaceutically effective amount of at least one compound of formula (I) as defined above, or one of its pharmaceutically acceptable addition salts, is incorporated in a pharmaceutically acceptable excipient, vehicle or carrier, it being possible for this pharmaceutical composition to be prepared advantageously in the form of hard gelatin capsules or tablets containing 1 to 400 mg of active principle or in the form of injections containing 0.01 to 50 mg of active principle.

The invention also covers a method for the therapeutic treatment of mammals, characterised in that a therapeutically effective amount of at least one compound of formula (I) as defined above, or one of its pharmaceutically acceptable addition salts, is administered to this mammal.

In animal therapy, the daily dose which can be used should normally lie between 1 and 100 mg per kg.

Other features and advantages of the invention will be more clearly understood on reading the description which follows of some examples of preparation, which are in no way limiting but given by way of illustration.

EXAMPLE 1

Ethyl 3-oxohexanoate

Formula (II): $R_1$=n-propyl $R_6$=ethyl 176 g of 2,2-dimethyl-4,6-dioxo-1,3-dioxane (Meldrum's acid) are dissolved in 550 ml of dichloromethane and 188 ml of pyridine. The mixture is cooled to 0° C. with a water/ice bath and 133 ml of butyryl chloride are added dropwise. When the addition is complete, the mixture is stirred for 3 hours at room temperature. The solution is washed with dilute hydrochloric acid solution, dried over magnesium sulphate and evaporated under vacuum to give an oil. This oil is dissolved in 700 ml of ethanol and the mixture is heated to reflux for 6 hours. The ethanol is evaporated off under vacuum and the residue obtained is distilled to give 145.4 g of ethyl 3-oxohexanoate in the form of a liquid of boiling point b.p.$_{20}$ 98°–100° C.

EXAMPLE 2

Ethyl 3-oxoheptanoate

Formula (II): $R_1$=n-butyl, $R_6$=ethyl
Prepared according to the procedure of Example 1.
Liquid of boiling point b.p.$_{20}$ 115°–120° C.

EXAMPLE 3

Ethyl 2-(4-nitrobenzyl)-3-oxohexanoate

Formula (IV): $R_1$=n-propyl V=$NO_2$ $R_6$=ethyl
127.7 g of ethyl 3-oxohexanoate are dissolved in 700 ml of tetrahydrofuran. 174.5 g of 4-nitrobenzyl bromide and 35 g of lithium chloride are added and the mixture is stirred at room temperature. 286 ml of diisopropylethylamine are then introduced dropwise, which causes a slight exothermic effect. The mixture is then stirred for 3 hours at room temperature and thereafter for 10 hours under reflux. The solvents are evaporated off under vacuum and the residue is taken up with water and then extracted with chloroform. The organic phase is separated after settling has taken place and then washed with dilute hydrochloric acid solution, dried over magnesium sulphate and evaporated under vacuum. The oily residue obtained is taken up with isopropyl ether and the crystals formed are filtered off. The mother liquors are concentrated under vacuum and the residue is heated to 130° C. at 20 mmol mercury in order to remove the residual starting materials. 174 g of ethyl 2-(4-nitrobenzyl)-3-oxohexanoate are thereby obtained in the form of an oil, which is used without further purification for the next step.

EXAMPLE 4

Ethyl 2-[(2'-cyano-4-biphenylyl)methyl]-3-oxohexanoate

Formula (IV): $R_1$=n-propyl, $R_6$=ethyl

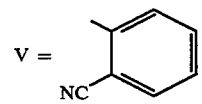

Prepared according to the procedure of Example 3, from 4'-bromomethyl-2-cyanobiphenyl.

Oil used without further purification for the next step.
Preparation of 4'-bromomethyl-2-cyanobiphenyl:

A) 4'-Methyl-2-cyanobiphenyl:

18.5 g of (4'-methyl-2-biphenylyl)carboxylic acid, prepared according to MEYERS, A. I. and MIHELICH, E. D.; J. Am. Chem. Soc., 1975, 97 (25), 7383, are heated to reflux in 60 ml of thionyl chloride for 2 hours. The thionyl chloride is concentrated under vacuum and the residue is poured into 28% ammonium hydroxide solution, the mixture is stirred for 30 minutes and the crystals obtained are drained and washed with ether and then dried to give 14.5 g of (4'-methyl-2-biphenylyl)carboxamide in the form of crystals of melting point 128° C. These crystals are taken up in 50 ml of thionyl chloride and the mixture is heated to reflux for 3 hours and then concentrated under vacuum to give 9 g of 4'-methyl-2-cyanobiphenyl in the form of crystals of melting point 45°–46° C.

B) 4'-Bromomethyl-2-cyanobiphenyl:

7.9 g of 4'-methyl-2-cyanobiphenyl, prepared in A), are dissolved in 100 ml of carbon tetrachloride in the presence of 7.3 g of N-bromosuccinimide and 0.3 g of benzoyl peroxide. The mixture is heated to reflux for 6 hours and the crystals are filtered off; the remaining solution is concentrated under vacuum and the residue is crystallised in ether to give 6.6 g of 4'-bromomethyl-2-cyanobiphenyl in the form of crystals of melting point 115°–118° C.

EXAMPLE 5

Ethyl 2-[(2'-cyano-4-biphenylyl)methyl]-3-oxoheptanoate

Formula (IV): $R_1$=n-butyl, $R_6$=ethyl,

V = 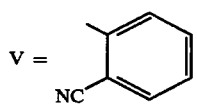

Prepared according to the procedure of Example 3. Oil used without further purification for the next step.

EXAMPLE 6

6-n-Propyl-2-methyl-4-hydroxy-5-(4-nitrobenzyl)-pyrimidine

Formula (VII): $R_1$=n-propyl, $R_2$=methyl, V=$NO_2$ 3.5 g of sodium are dissolved in 175 ml of ethanol. 9.5 g of acetamidine hydrochloride are added to this solution and the mixture is stirred for 5 minutes at room temperature. 20 g of ethyl 2-(4-nitrobenzyl)-3-oxohexanoate, prepared in Example 3, are then added and the mixture is stirred for 4 days at room temperature. The solvents are then evaporated off under vacuum and the residue is taken up with hydrochloric acid solution and extracted with ethyl acetate. The organic phase is dried over magnesium sulphate and then evaporated under vacuum to give an oily residue which crystallises in an acetone/ether mixture. The crystals are drained and dried and give 10.9 g of 6-n-propyl-2-methyl-4-hydroxy-5-(4-nitrobenzyl)pyrimidine in the form of crystals of melting point 200° C.

EXAMPLE 7

6-n-Propyl-2-methyl-4-hydroxy-5-[(2'-cyano-4-biphenylyl)methyl]pyrimidine

Formula (VII): $R_1$=n-propyl, $R_2$=methyl,

V = 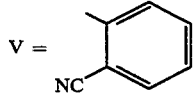

Prepared according to the procedure of Example 6. Crystals of melting point 206° C.

EXAMPLE 8

6-n-Butyl-2-methyl-4-hydroxy-5-[(2'-cyano-4-biphenylyl)methyl]pyrimidine

Formula (VII): $R_1$=n-butyl, $R_2$=methyl,

V = 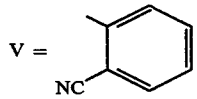

Prepared according to the procedure of Example 6. Crystals of melting point 173° C.

EXAMPLE 9

6-n-Propyl-2-methyl-5-(4-nitrobenzyl)-4-chloropyrimidine

Formula (VIII): $R_1$=n-propyl, $R_2$=methyl, V=$NO_2$ 32 g of 6-n-propyl-2-methyl-5-(4-nitrobenzyl)-4-hydroxypyrimidine, prepared in Example 6, are suspended in 45 ml of phosphorus oxychloride. The mixture is brought to reflux for 6 hours and then concentrated under vacuum. The residue is taken up with water and extracted with dichloromethane. The organic phase is washed with potassium carbonate solution, then dried over magnesium sulphate and evaporated to dryness to give 24 g of 6-n-propyl-2-methyl-5-(4-nitrobenzyl)-4-chloropyrimidine in the form of crystals of melting point 65° C.

EXAMPLE 10

6-n-Propyl-2-methyl-4-chloro-5-[(2'-cyano-4-biphenylyl)methyl]pyrimidine

Formula (VIII): $R_1$=n-propyl, $R_2$=methyl,

V = 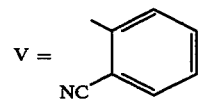

Prepared according to the procedure of Example 9. Crystals of melting point 95° C.

EXAMPLE 11

6-n-Butyl-2-methyl-4-chloro-5-[(2'-cyano-4-biphenylyl)methyl]pyrimidine

Formula (VIII): $R_1$=n-butyl, $R_2$=methyl,

V = 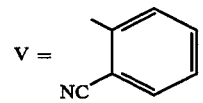

Prepared according to the procedure of Example 9. Crystals of melting point 75° C.

EXAMPLE 12

6-n-Propyl-2-methyl-4-hydrazino-5-[(2'-cyano-4-biphenylyl)methyl]pyrimidine

Formula (IX): $R_1$=n-propyl, $R_2$=methyl,

V = 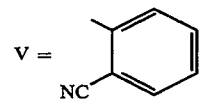

51.7 g of 6-n-propyl-2-methyl-4-chloro-5-[(2'-cyano-4-biphenylyl)methyl]pyrimidine, prepared in Example 10, are dissolved in 150 ml of ethanol and 90 ml of hydrazine hydrate. The mixture is heated to reflux for 6 hours and the solvent is concentrated to one half under vacuum and then treated with water. The crystals formed are drained, washed with water and then with ether and dried to give 46 g of 6-n-propyl-2-methyl-4-hydrazino-5-(2'-cyano-4-biphenylyl)methyl]pyrimidine in the form of crystals of melting point 156° C.

EXAMPLE 13

6-n-Propyl-2-methyl-4-hydrazino-5-(4-nitrobenzyl)-pyrimidine

Formula (IX): $R_1$=n-propyl, $R_2$=methyl, V=$NO_2$
Prepared according to the procedure of Example 12. Crystals of melting point 126° C.

EXAMPLE 14

6-n-Butyl-2-methyl-4-hydrazino-5-[(2'-cyano-4-biphenylyl)methyl]pyrimidine Formula (IX):
$R_1$=n-butyl, $R_2$=methyl, V = 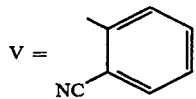

Prepared according to the procedure of Example 12. Crystals of melting point 154° C.

EXAMPLE 15

7-n-Propyl-5-methyl-8-[(2'-cyano-4-biphenylyl)methyl]-1,2,4-triazolo[4,3-c]pyrimidin-3(2H)-one Formula (XII): $R_1$=n-propyl, $R_2$=methyl, X—CO, V = 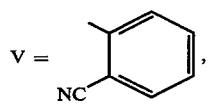, Y=NH, X···Y=single bond 33.4 g of 6-n-propyl-2-methyl-4-hydrazino-5-[(2'-cyano-4-biphenylyl)methyl]pyrimidine, prepared in Example 12, are dissolved in 600 ml of tetrahydrofuran. 15.2 g of carbonyldiimidazole are added and the mixture is heated to reflux for 1 h 30 min. The solvent is evaporated off under vacuum and the residue is taken up with water and then extracted with chloroform. The organic phase is dried over magnesium sulphate and evaporated under vacuum; the residue obtained crystallises in an ether/ethyl acetate mixture to give 26.4 g of 7-n-propyl-5-methyl-8-[(2'-cyano-4-biphenylyl)methyl]-1,2,4-triazolo-[4,3-c]pyrimidin-3(2H)-one in the form of crystals of melting point 196° C.

EXAMPLE 16

7-n-Propyl-5-methyl-8-(4-nitrobenzyl)-1,2,4-triazolo[4,3-c]pyrimidin-3(2H)-one

Formula (XII): $R_1$=n-propyl, $R_2$=methyl, X=CO, Y=NH, X···Y=single bond, V=NO$_2$ Prepared according to the procedure of Example 15. Crystals of melting point 225° C.

EXAMPLE 17

7-n-Butyl-5-methyl-8-[(2'-cyano-4-biphenylyl)methyl]-1,2,4-triazolo[4,3-c]pyrimidin-3(2H)-one Formula (XII): $R_1$=n-butyl, $R_2$=methyl, X=CO, Y=NH, X···Y=single bond, V = 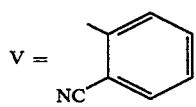

Prepared according to the procedure of Example 15. Crystals of melting point 173° C.

EXAMPLE 18

7-n-Propyl-5-methyl-8- [(2 '-cyano-4-biphenylyl)methyl]- 1,2,4 -triazolo [1,5 -c]pyrimidin-2 (3H )-one Formula (XII): $R_1$=n-propyl, $R_2$=—methyl, Y=CO, X=NH, X···Y=single bond, V = 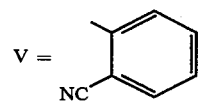

13.8 g of 7-n-propyl-5-methyl-8-[(2'cyano-4-biphenylyl)methyl]-1,2,4-triazolo[4,3-c]pyrimidin-3(2H)-one, prepared in Example 125, are dissolved in 40 ml of ethanol and 150 ml of 3 N potassium hydroxide solution. The mixture is heated to 60° C. for 4 hours and 100 ml of water are then added. The solution is acidified with concentrated hydrochloric acid and the crystals obtained are drained, washed with water and taken up in chloroform. The chloroform solution is dried over magnesium sulphate and evaporated under vacuum. The residue obtained crystallises in an ethyl acetate/ether mixture to give 10.6 g of crystals, which are chromatographed on silica gel with a 9:1 chloroform-/methanol eluent to give 8.4 g of 7-n-propyl-5-methyl-8-[(2'-cyano-4-biphenylyl)methyl]-1,2,4-triazolo[1,5-c]pyrimidin-2(3H)-one in the form of crystals of melting point 226° C.

EXAMPLE 19

7-n-Propyl-5-methyl-8-{[2'-(5-tetrazolyl)-4-biphenylyl]-methyl}-1,2,4-triazolo[4,3-c]pyrimidin-3(2H)-one Formula (I): $R_1$=n-propyl, $R_2$=methyl, X=CO, Y=NH, X···Y=single bond, $R_3$ = 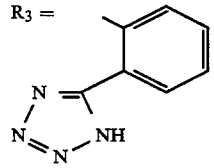

4 g of 7-n-propyl-5-methyl-8-[(2'-cyano-4-biphenylyl)methyl]-1,2,4-triazolo[4,3-c]pyrimidin-3(2H)-one, prepared in Example 15, are dissolved in 100 ml of toluene. 2.8 g of trimethyltin azide are added and the mixture is heated to reflux for 24 hours. The crystals formed are drained in the heated state and washed with ether, then suspended in 100 ml of tetrahydrofuran. Hydrogen chloride gas is bubbled into the mixture and, after the reactants have passed completely into solution, a precipitate appears. The mixture is left overnight at room temperature and the crystals formed are drained, washed with ether and dissolved in dilute sodium hydroxide solution. This solution is washed with ether, then acidified by bubbling in sulphur dioxide and extracted with chloroform. The organic phase is dried over magnesium sulphate and evaporated under vacuum, and the residue crystallises in an ether/acetone mixture to give 1.5 g of 7-n-propyl-5-methyl-8-{[2'-(5-tetrazolyl)-4-biphenylyl]methyl}-1,2,4-triazolo[4,3-c]pyrimidin-(3(2H)-one in the form of crystals of melting point 248°-249° C.

EXAMPLE 20

7-n-Propyl-5-methyl-8-{[2'-(5-tetrazolyl)-4-biphenylyl]-methyl}-1,2,4-triazolo[1,5-c]pyrimidin-2(3H)-one Formula (I): R$_1$=n-propyl, R$_2$=methyl, X=NH, Y=CO, X···Y=single bond,

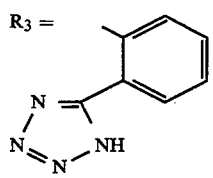

Prepared according to the procedure of Example 19, from the compound of Example 18.

May also be prepared according to the procedure of Example 18, from the compound of Example 19.

Recrystallised in acetic acid and then washed with ethyl acetate.

Crystals of melting point 239° C.

EXAMPLE 21

Ethyl {7-n-propyl-5-methyl-3-oxo-8-[(2'-cyano-4-biphenylyl)-methyl]-2,3-dihydro-1,2,4-triazolo[4,3-c]pyrimidin-2-yl}acetate Formula (XII): R$_1$=n-propyl, R$_2$=methyl, X=CO, Y=N CH$_2$CO$_2$Et, X···Y=single bond,

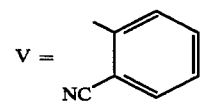

3.8 g of 7-n-propyl-5-methyl-8-[(2'-cyano-4-biphenylyl)methyl]-1,2,4-triazolo[4,3-c]pyrimidin-3(2H)-one, prepared in Example 15, are dissolved in 50 ml of ethanol. A solution of sodium ethylate, prepared from 0.25 g of sodium in 10 ml of ethanol, is added and the mixture is stirred for 10 minutes at room temperature. 1.3 ml of ethyl bromoacetate are added and the mixture is heated to reflux for 7 hours. The solvent is concentrated under vacuum and the residue is taken up with water and extracted with ether. The organic phase is washed with cold dilute sodium hydroxide solution, then dried and evaporated under vacuum to give 4.3 g of ethyl {7-n-propyl-5-methyl-8-[(2'-cyano-4-biphenylyl)methyl]-3-oxo-2,3-dihydrotriazolo[4,3-c]pyrimidin-2-yl}acetate in the form of an oil, which is used without further purification for the next step.

EXAMPLE 22

Ethyl[7-n-propyl-5-methyl-3-oxo-8-{[2,-(5-tetrazolyl)-4-biphenylyl]methyl}-2,3-dihydro-1,2,4-triazolo[4,3-c]pyrimidin-2-yl]acetate Formula (I): R$_1$=n-propyl, R$_2$=methyl, X=CO, Y=N CH$_2$CO$_2$Et, X···Y=single bond,

Prepared according to the procedure of Example 19. Crystals of melting point 173°–174° C.

EXAMPLE 23

2-{7-n-Propyl-5-methyl-3-oxo-8-[(2'-cyano-4-biphenylyl)methyl]-2,3-dihydro-1,2,4-triazolo[4,3-c]pyrimidin-2-yl}ethanol Formula (XII): R$_1$=n-propyl, R$_2$=methyl, X=CO, Y=N CH$_2$CH$_2$OH, X···Y=single bond

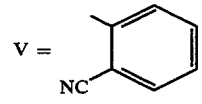

Prepared according to the procedure of Example 21, from 2-bromoethanol.

Crystals of melting point 112° C.

EXAMPLE 24

7-n-propyl-2,5-dimethyl-8-[(2'-cyano-4-biphenylyl)methyl]-1,2,4-triazolo[4,3-c]pyrimidin-3(2H)-one Formula (XII): R$_1$=n-propyl, R$_2$=methyl, X=CO, Y=NCH$_3$, X···Y=single bond,

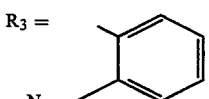

Prepared according to the procedure of Example 21, from methyl iodide.

Crystals of melting point 145° C.

EXAMPLE 25

2-[7-n-Propyl-5-methyl-3-oxo-8-{[2'-(5-tetrazolyl)-4-biphenylyl]methyl}-2,3-dihydro-1,2,4-triazolo[4,3-c]pyrimidin-2-yl]ethanol Formula (I): R$_1$=n-propyl, R$_2$=methyl, X=CO, Y=N CH$_2$CH$_2$OH, X···Y=single bond, Prepared according to the procedure of Example 19. Crystals of melting point 149°–150° C.

EXAMPLE 26

7-n-Propyl-2,5-dimethyl-8-{[2-(5-tetrazolyl)-4-biphenylyl]methyl}-1,2,4-triazolo[4,3-c]pyrimidin-3(2H)-one Formula (I): $R_1$=n-propyl, $R_2$=methyl, X=CO, Y=NCH$_3$, X···Y=single bond,

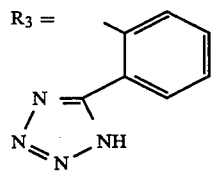

Prepared according to the procedure of Example 19. Crystals of melting point 205°–206° C.

EXAMPLE 27

7-n-propyl-5-methyl-2-methoxy-8-[(2'-cyano-4-biphenylyl)methyl]-1,2,4-triazolo[1,5-c]pyrimidine Formula (XII): $R_1$=n-propyl, $R_2$=methyl, X=N, Y=C—OCH$_3$, X···Y=double bond

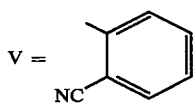

4.4 g of 7-n-propyl-5-methyl-8-[(2'-cyano-4-biphenylylmethyl]pyrimidin-2 (3H) -one, prepared in Example 18, are dissolved in 50 ml of acetone, and 2 g of potassium carbonate are added. After the addition of 2 ml of methyl iodide, the mixture is brought to reflux for 5 hours, cooled and concentrated under vacuum, then treated with water and extracted with dichloromethane. The organic phase is dried over magnesium sulphate and evaporated under vacuum, and the residue is chromatographed on silica gel in an 80:20 chloroform/acetone eluent to give 3 g of 7-n-propyl-5-methyl-2-methoxy-8-(2'-cyano-4-biphenylyl)methyl]-1,2,4-triazolo[1,5-c]pyrimidine (first product eluted) in the form of crystals of melting point 89° C.

EXAMPLE 28

7-n-propyl-5-methyl-2-methoxy-8-{[2,-(5-tetrazolyl)-4-biphenylyl]methyl}-1,2,4-triazolo[1,5-c]pyrimidine Formula (I): $R_1$=n-propyl, $R_2$=methyl, X=N, Y=-C—OCH$_3$, X···Y=double bond,

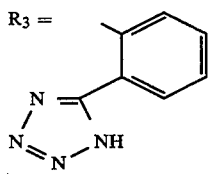

Prepared according to the procedure of Example 19. Crystals of melting point 189°–190° C.

EXAMPLE 29

7-n-Propyl-3,5-dimethyl-B-[(2'-cyano-4-biphenylyl)methyl]-1,2,4-triazolo[1,5-c]pyrimidin-2(3H)-one Formula (XII): $R_1$=n-propyl, $R_2$=methyl, X=N—CH$_3$ Y=CO, X···Y=single bond,

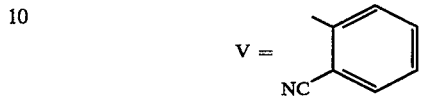

Prepared according to the procedure of Example 27 and purified by chromatography on silica gel with a 90:10 chloroform/methanol eluent (second product eluted).

Crystals of melting point 194° C.

EXAMPLE 30

7-n-propyl-5-methyl-B-(4-aminobenzyl)-1,2,4-triazolo[4,3-c]pyrimidin-3(2H)-one

Formula (XII): $R_1$=n-propyl, $R_2$=methyl, X=CO, Y=NH, X···Y=single bond, V=NH$_2$ 5.4 g of 7-n-propyl-5-methyl-8-(4-nitrobenzyl)-1,2,4-triazolo[4,3-c]pyrimidin-3(2H)-one, prepared in Example 16, are dissolved in 100 ml of methanol and hydrogenated at atmospheric pressure and room temperature in the presence of 0.8 g of Raney nickel. When the uptake of hydrogen has ceased, the catalyst is filtered off and the solvent evaporated off under vacuum to give 4.6 g of 7-n-propyl-5-methyl-8-(4-aminobenzyl)-1,2,4-triazolo[4,3c]pyrimidin-3(2H)-one in the form of crystals of melting point 180° C.

EXAMPLE 31

2-[{4-[7-n-Propyl-5-methyl-3-oxo-2,3-dihydro-1,2,4-triazolo[4,3-c]pyrimidin-8-yl)methyl]phenyl}aminocarbonyl]benzenesulphonic acid Formula (I): $R_1$=n-propyl, $R_2$=methyl, X=CO, Y=NH, X···Y=single bond,

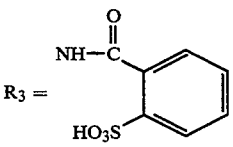

4.6 g of 7-n-propyl-5-methyl-8-(4-aminobenzyl)-1,2,4-triazolo[4,3-c]pyrimidin-3(2H)-one, prepared in Example 30, are dissolved in 300 ml of acetonitrile, and a solution of 2.9 g of sulphobenzoic anhydride in 30 ml of acetonitrile is added. The mixture is stirred for 15 minutes and the crystals formed are drained and washed with ether, then dissolved in aqueous sodium bicarbonate solution. The aqueous phase is then acidified by bubbling sulphur dioxide in to give 4 g of 2-[{4-[(7-n-propyl-5-methyl-3-oxo-2,3-dihydro-1,2,4-triazolo[4,3-c]pyrimidin-yl)methyl]phenyl}aminocarbonyl]benzenesulphonic acid in the form of crystals of melting point 283°–286° C.

EXAMPLE 32

Ethyl[7-n-propyl-5-methyl-3-oxo-8-(4-nitrobenzyl)-2,3-dihydro-1,2,4-triazolo[4,3-c]pyrimidin-2-yl]acetate Formula (XII): $R_1$=n-propyl, $R_2$=methyl, X=CO, Y=N CH$_2$CO$_2$Et, X···Y=single bond, V=NO$_2$ Prepared according to the procedure of Example 21. Crystals of melting point 144° C.

EXAMPLE 33

Ethyl [7 -n-propyl-5-methyl-3-oxo-8-(4-aminobenzyl)-2,3-dihydro- 1,2,4-triazolo[4,3-c]pyrimidin-2-yl ]acetate Formula (XI I): $R_1$=n-propyl, $R_2$=methyl, X =CO, Y=N CH$_2$CO$_2$Et, X···Y=single bond, V=NH$_2$ Prepared according to the procedure of Example 30. Crystals of melting point 130° C.

EXAMPLE 34

2-{[4-{[7-n-Propyl-5-methyl-3-oxo-2-(ethoxycarbonylmethyl)-2,3-dihydro-1,2,4-triazolo[4,3-c]pyrimidin-8-yl]methyl}phenyl]aminocarbonyl}benzenesulphonic acid Formula (I ): $R_1$=n-propyl, $R_2$=methyl, X=CO, Y=N CH$_2$CO$_2$Et, X···Y=single bond,

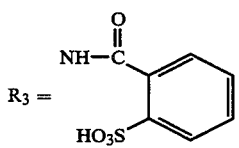

Prepared according to the procedure of Example 31. Crystals of melting point 282-284° C.

EXAMPLE 35

2-{[4-{[7-n-Propyl-5-methyl-3-oxo-2-(carboxymethyl)-2,3-dihydro-1,2,4-triazolo 8 4 , 3-c ]pyrimidin-8-yl]methyl}phenyl]aminocarbonyl}-benzenesulphonic acid Formula (I): $R_1$=n-propyl, $R_2$=methyl, X=CO, Y=NCH$_2$CO$_2$H, X···Y=single bond,

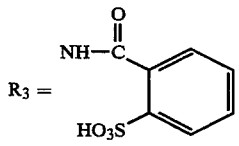

2.5 g of 2- {[4 - {[7 -n-propyl-5-methyl- 3-oxo-2-(ethoxycarbonylmethyl)-2,3-dihydro-1,2,4-triazolo[4,3-c]-pyrimidin- 8-Yl]methyl}phenyl]aminocarbonyl}benzenesulphonic acid, prepared in Example 34, are dissolved in 30 ml of water containing 1 g of sodium hydroxide. The mixture is heated to 60° C. for 2 hours, cooled and acidified with hydrochloric acid to give 2 g of 2-{[4-{[7-n-propyl-5-methyl-3-oxo-2-(carboxymethyl)-2,3-dihydro-1,2,4-triazolo[4,3-c]pyrimidin-8-yl]methyl}phenyl]-aminocarbonyl}benzenesulphonic acid in the form of crystals of melting point 296°-300° C.

EXAMPLE 36

7-n-Butyl-5-methyl-8-{[2'-(5-tetrazolyl)-4-biphenylyl]-methyl}-1,2,4-triazolo[4,3-c]pyrimidin-3(2H)-one Formula (I): $R_1$=n-butyl, $R_2$=methyl, X=CO, Y=NH, X···Y=single bond,

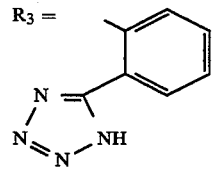

Prepared according to the procedure of Example 19. Crystals of melting point 233°-235° C.

EXAMPLE 37

7-n-Propyl-5-methyl-2-mercapto-8-(4-nitrobenzyl)-1,2,4-triazolo[1,5-c]pyrimidine Formula (XII): $R_1$=n-propyl, $R_2$=methyl, X=N, Y=C—SH, X···Y=double bond V=NO$_2$ 3.7 g Of 6-n-propyl-2-methyl-4-hydrazino-5-(4-nitrobenzyl)pyrimidine, prepared in Example 13, are dissolved in 50 ml of n-butanol in the presence of 1.5 ml of carbon disulphide. The mixture is heated under reflux for 3 hours and then cooled, and the crystals obtained are drained and washed with ether and then dried to give 3.5 g of 7-n-propyl-5-methyl-2-mercapto-8-(4-nitrobenzyl)-1,2,4-triazolo[1,5-c]pyrimidine in the form of crystals of melting point 210° C.

EXAMPLE 38

7-n-Propyl-5-methyl-2-methylmercapto-8-(4-nitrobenzyl)-1,2,4-triazolo[1,5-c]pyrimidine Formula (XII): $R_1$=n-propyl, $R_2$=methyl, X=N, Y=C-SCH$_3$, X···Y=double bond V=NO$_2$ 5 g of 7-n-propyl-5-methyl-2-mercapto-8-(4-nitrobenzyl)-1,2,4-triazolo[1,5-c]pyrimidine, prepared in Example 37, are dissolved in 50 ml of chloroform and 2.2 ml of triethylamine. 1.5 ml of methyl iodide are added and the mixture is stirred at room temperature for 2 hours and then left overnight. The mixture is then washed with dilute sodium hydroxide solution and the organic phase is separated after settling has taken place, dried over magnesium sulphate and evaporated under vacuum to give a residue which crystallise in an ether/pentane mixture to yield 4 g of 7-n-propyl-5-methyl-2-methylmercapto-8-(4-nitrobenzyl)-1,2,4triazolo[1,5-c]pyrimidine in the form of crystals of melting point 130° C.

EXAMPLE 39

7-n-Propyl-5-methyl-2-methylmercapto-8-(4-aminobenzyl)-1,2,4-triazolo[1,5-c]pyrimidine Formula (XII): $R_1$=n-propyl, $R_2$=methyl, X=N, Y=C—SCH$_3$, X···Y=double bond V=NH$_2$ Prepared according to the procedure of Example 30. Oil used without further purification for the next step.

EXAMPLE 40

2-[{4-[(7-n-Propyl-5-methyl-2-methylmercapto-1,2,4-triazolo[1,5-c]pyrimidin-8-yl)methyl]phenyl}aminocarbonyl]benzenesulphonic acid Formula (I): R$_1$=n-propyl, R$_2$=methyl, X=N, Y=-C—SCH$_3$, X···Y—double bond R$_3$ = 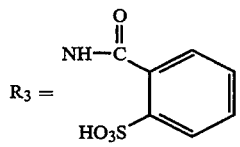

Prepared according to the procedure of Example 31. Crystals of melting point 250°-252° C.

EXAMPLE 41

7-n-Propyl-5-methyl-2-mercapto-8-[(2'-cyano-4-biphenylyl)methyl]-1,2,4-triazolo[1,5-c]pyrimidine Formula (XII): R$_1$=n-propyl, R$_2$=methyl, X=N, Y=C—SH, X···Y=double bond V = 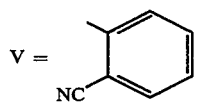

Prepared according to the procedure of Example 37. Crystals of melting point 202° C.

EXAMPLE 42

7-n-propyl-5-methyl-2-mercapto-8-{[2'-(5-tetrazolyl)-4-biphenylyl]methyl}-1,2,4-triazolo[1,5-c]pyrimidine Formula (I): R$_1$=n-propyl, R$_2$=methyl, X=N, Y=-C—SH, X···Y=double bond, R$_3$ = 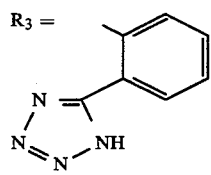

Prepared according to the procedure of Example 19. Crystals of melting point 223°-225° C.

EXAMPLE 43

Ethyl {7-n-propyl-5-methyl-8-[(2'-cyano-4-biphenylyl)methyl]-1,2,4-triazolo[1,5-c]pyrimidin-2-yl}mercaptoacetate Formula (XII): R$_1$=n-propyl, R$_2$=methyl, X=N, Y=C—SCH$_2$—CO$_2$—Et, X···Y=double bond V = 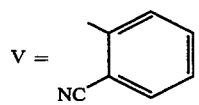

4 g of 7-n-propyl-5-methyl-8-[(2'-cyano-4-biphenylyl)methyl]-2-mercapto-1,2,4-triazolo[1,5-c]pyrimidine, prepared in Example 41, are dissolved in 40 ml of ethanol, and a solution of sodium ethylate, obtained by adding 0.3 g of sodium to 5 ml of ethanol, is added. The mixture is stirred for 10 minutes at room temperature, and 1.5 ml of ethyl bromoacetate are added. The mixture is then brought to reflux for 2 hours, the solvent is thereafter evaporated under vacuum and the residue is taken up with water and extracted with ethyl acetate. The organic phase is dried over magnesium sulphate and evaporated under vacuum, and the residue obtained crystallises in an ether/pentane mixture to give 2.9 g of ethyl {7-n-propyl-5-methyl-8-[(2'-cyano-4-biphenylyl)methyl]-1,2,4-triazolo[1,5-c]pyrimidin-2-yl}mercaptoacetate in the form of crystals of melting point 103° C.

EXAMPLE 44

Ethyl [7-n-propyl-5-methyl-8-{[2'-(5-tetrazolyl)-4-biphenylyl]methyl}-1,2,4-triazolo[1,5-c]pyrimidin-2-yl]mercaptoacetate Formula (I): R$_1$=n-propyl, R$_2$=methyl, X=N, Y=-C—SCH$_2$CO$_2$Et, X···Y=double bond, R$_3$ = 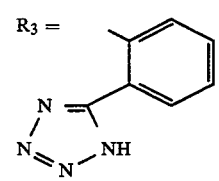

Prepared according to the procedure of Example 19. Crystals of melting point 127°-8° C.

EXAMPLE 45

{7-n-Propyl-5-methyl-8-[(2'-cyano-4-biphenylyl)methyl]-1,2,4-triazolo[1,5-c]pyrimidin-2-yl}sulphonyl chloride Formula (XII): R$_1$=n-propyl, R$_2$=methyl, X=N, Y=C—SO$_2$Cl, X···Y=double bond, V = 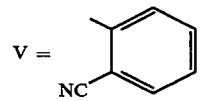

35 g of 7-n-propyl-5-methyl-2-mercapto-8-[(2'-cyano-4-biphenylyl)methyl]-1,2,4-triazolo[1,5c]pyrimidine, prepared in Example 41, are dissolved at −5° C. in 300 ml of concentrated hydrochloric acid. 13 g of sodium chloride, dissolved in 50 ml of water, are added dropwise in the course of 15 minutes, the temperature being maintained at between -5° C. and 0° C. The mixture is then stirred for 20 minutes at 0° C. and thereafter poured into an ice/water mixture; the crystals formed are drained and washed with water, then taken up in 250 ml of ether and stirred for five minutes, and then drained and dried in the air to give 30 g of {7-n-propyl-5-methyl-8-[(2'-cyano-4-biphenylyl)methyl]-1,2,4-triazolo[1,5-c]pyrimidin-2-yl}sulphonyl chloride in the form of crystals of melting point 141° C.

EXAMPLE 46

{7-n-Butyl-5-methyl-8-[(2'-cyano-4-biphenylyl)methyl]-1,2,4-triazolo[1,5-c]pyrimidin-2-yl}sulphonyl chloride Formula (XII): $R_1$=n-butyl, $R_2$=methyl, X=N, Y=C—SO$_2$Cl, X···Y=double bond,

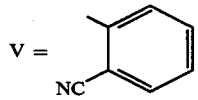

Prepared according to the procedure of Example 45. Crystals of melting point 112° C.

EXAMPLE 47

N,N-Dimethyl-{7-n-propyl-5-methyl-8-[(2'-cyano-4-biphenylyl)methyl]-1,2,4-triazolo[1,5-c]pyrimidin-2-yl}sulphonamide Formula (XII): $R_1$=n-propyl, $R_2$=methyl, X=N, Y=C—SO$_2$N(CH$_3$)$_2$ X···Y=double bond,

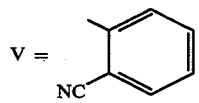

8 g of {7-n-propyl-5-methyl-8-[(2'-cyano-4-biphenylyl)-methyl]-1,2,4-triazolo[1,5-c]pyrimidin-2-yl}sulphonyl chloride, prepared in Example 45, are stirred with 40 ml of a 40% aqueous solution of dimethylamine for one hour at 50° C. The mixture is then extracted with chloroform, and the organic phase is dried over magnesium sulphate and then concentrated under vacuum to give 5.5 g of N,N-dimethyl-{7-n-propyl-5-methyl-8-[(2'-cyano-4-biphenylyl)methyl]-1,2,4-triazolo[1,5-c]pyrimidin-2-yl}sulphonamide in the form of crystals of melting point 158° C. The following examples were prepared according to the same procedure:

EXAMPLE 48

N-Methyl-{7-n-propyl-5-methyl-8-[(2'-cyano-4-biphenylyl)methyl]-1,2,4-triazolo[1,5-c]pyrimidin-2-yl}sulphonamide Formula(XII): $R_1$=n-propyl, $R_2$=methyl, X=N, Y=C—SO$_2$NH CH$_3$ X···Y=double bond,

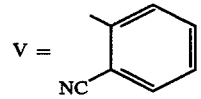

Crystals of melting point 172 ° C.

EXAMPLE 49

N,N-Dimethyl-{7-n-butyl-5-methyl-8- [(2 '-cyano-4-biphenylyl ) methyl ]- 1,2,4 -triazolo[1,5-c ]pyrimidin-2-yl}sulphonamide Formula (XII): $R_1$=n-butyl, $R_2$=methyl, X=N, Y=C—SO$_2$N (CH$_3$)$_2$ X···Y=double bond,

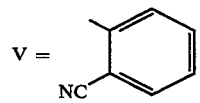

Crystals of melting point 126° C.

EXAMPLE 50

{7-n-Propyl-5-methyl-8- [(2 -cyano-4-biphenylyl)methyl]-1,2,4-triazolo [1,5-c]pyrimidin-2 -yl }sulphonamide Formula (XII): $R_1$=n-propyl, $R_2$=methyl, X=N, Y=C—SO$_2$NH$_2$ X···Y=double bond,

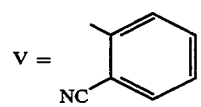

Oil used without further purification for the next step.

EXAMPLE 51

N-Methyl-{7-n-butyl-5-methyl-8-[(2'-cyano-4-biphenylyl)methyl]-1,2,4-triazolo[1,5-c]pyrimidin-2 -yl }sulphonamide Formula (XII): $R_1$=n-butyl, $R_2$=methyl, X=N, Y=C—SO$_2$NH CH$_3$, X···Y=double bond,

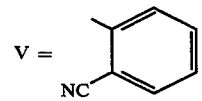

Crystals of melting point 149° C.

EXAMPLE 52

N,N-Dimethyl- [7 -n-propyl-5-methyl-8- {[2 '-(5-tetrazolyl ) -4-biphenylyl ]methyl }-1,2,4-triazolo[1,5-c ]pyrimidin-2-yl$_3$ sulphonamide Formula (I ): $R_1$=n-propyl, $R_2$=methyl, X=N, Y=-C—SO$_2$N(CH$_3$)$_2$, X···Y=double bond,

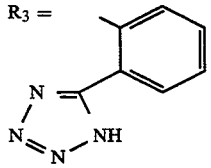

Prepared according to the procedure of Example 19. Crystals of melting point 176°–178° C.

EXAMPLE 53

N-Methyl-[7-n-propyl-5-methyl-8-{[2'-(5-tetrazolyl)-4-biphenylyl]methyl}-1,2,4-triazolo[1,5-c ]pyrimidin-2 -yl$_3$ sulphonamide Formula (I ): $R_1$=n-propyl, $R_2$=methyl, X=N, Y=-C—SO$_2$NHCH$_3$, X···Y =double bond, R₃ = 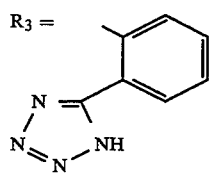

Prepared according to the procedure of Example 19. Crystals of melting point 163°–164° C.

EXAMPLE 54

[7-n-Propyl-5-methyl-8-{[2'-(5-tetrazolyl)-4-biphenylyl]methyl}-1,2,4-triazolo[1,5-c]pyrimidin-2-yl]sulphonamide Formula (I): $R_1$=n-propyl, $R_2$=methyl, X=N, Y=-C—$SO_2NH_2$, X···Y=double bond, R₃ = 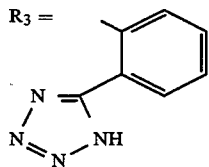

Prepared according to the procedure of Example 19. Crystals of melting point 200°–201° C.

EXAMPLE 55

N,N-Dimethyl-E7-n-Butyl-5-methyl-8-{[2'-(5-tetrazolyl)-4-biphenylyl]methyl}-1,2,4-triazolo[1,5-c]pyrimidin-2-yl]sulphonamide Formula (I): $R_1$=n-butyl, $R_2$=methyl, X=N, Y=-C—$SO_2N(CH_3)_2$, X···Y=double bond, R₃ = 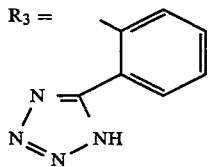

Prepared according to the procedure of Example 19. Crystals of melting point 147°–149° C.

EXAMPLE 56

N-Methyl-[-n-Butyl-5-methyl-8-{[2'-(5-tetrazolyl)-4-biphenylyl]methyl}-1,2,4-triazolo[1,5-c]pyrimidin-2-yl]sulphonamide Formula (I): $R_1$=n-butyl, $R_2$=methyl, X=N, Y=-C—$SO_2NHCH_3$, X···Y=double bond, R₃ = 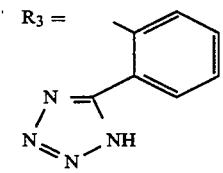

Prepared according to the procedure of Example 19. Crystals of melting point 179°–180° C.

EXAMPLE 57

7-n-Propyl-5-methyl-2-methylmercapto-8-[(2'-cyano-4-biphenylyl)methyl]-1,2,4-triazolo[1,5-c]pyrimidine Formula (XII): $R_1$=n-propyl, $R_2$=methyl, X=N, Y=C—$SCH_3$ X···Y=double bond, V = 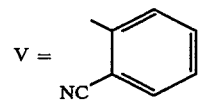

Prepared according to the procedure of Example 38. Crystals of melting point 107° C.

EXAMPLE 58

7-n-Butyl-5-methyl-2-methylmercapto-8-[(2'-cyano-4-biphenylyl)methyl]-1,2,4-triazolo[1,5-c]pyrimidine Formula (XII): $R_1$=n-butyl, $R_2$=methyl, X=N, Y=C—$SCH_3$ X···Y=double bond, V = 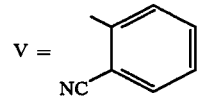

Prepared according to the procedure of Example 38. Oil used without further purification for the next step.

EXAMPLE 59

7-n-Propyl-5-methyl-2-methylmercapto-8-{[2'-(5-tetrazolyl)-4-biphenylyl]methyl}-1,2,4-triazolo[1,5-c]pyrimidine Formula (I): $R_1$=n-propyl, $R_2$=methyl, X=N, Y=-C—$SCH_3$, X···Y=double bond, R₃ = 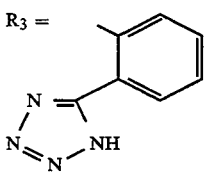

Prepared according to the procedure of Example 19. Crystals of melting point 169°–170° C.

EXAMPLE 60

7-n-Butyl-5-methyl-2-methylmercapto-8-{[2'-(5-tetrazolyl)-4-biphenylyl]methyl}-1,2,4-triazolo[1,5-c]pyrimidine Formula (I): $R_1$=n-butyl, $R_2$=methyl, X=N, Y=-C—$SCH_3$, X···Y=double bond, R₃ = 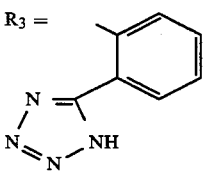

Prepared according to the procedure of Example 19. Crystals of melting point 194°–195° C.

EXAMPLE 61

7-n-Butyl-5-methyl-2-methoxy-8-[(2'-cyano-4-biphenylyl)methyl]-1,2,4-triazolo[1,5-c]pyrimidine Formula (XII): $R_1$=n-butyl, $R_2$=methyl, X=N, Y=C—OCH$_3$, X···Y=double bond,

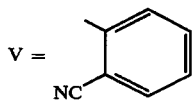

Prepared according to the procedure of Example 27. Crystals of melting point 88° C.

EXAMPLE 62

7-n-Butyl-5-methyl-2-methoxy-8-{[2'-(5-tetrazolyl)-4-biphenylyl]methyl}-1,2,4-triazolo[1,5-c]pyrimidine Formula (I): $R_1$=n-butyl, $R_2$=methyl, X=N, Y=-C—OCH$_3$, X···Y=double bond,

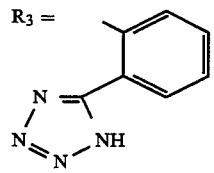

Prepared according to the procedure of Example 19. Crystals of melting point 195°–196° C.

EXAMPLE 63

Ethyl {7-n-butyl-5-methyl-3-oxo-8-[(2'-cyano-4-biphenylyl)methyl]-2,3-dihydro-1,2,4-triazolo[4,3-c]pyrimidin-2-yl}acetate Formula (XII): $R_1$=n-butyl, $R_2$=methyl, X=CO, Y=N—CH$_2$—CO$_2$Et, X···Y=single bond,

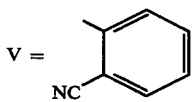

Prepared according to the procedure of Example 21. Oil used without further purification for the next step.

EXAMPLE 64

Ethyl [7-n-butyl-5-methyl-3-oxo-8-{[2'-(5-tetrazolyl)-4-biphenylyl]methyl}-2,3-dihydro-1,2,4-triazolo[4,3-c]pyrimidin-2-yl]acetate Formula (I): $R_1$=n-butyl, $R_2$=methyl, X=CO, Y=N-CH$_2$-CO$_2$Et, X···Y=single bond,

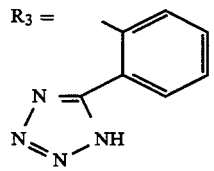

Prepared according to the procedure of Example 19. Crystals of melting point 174°–175° C.

EXAMPLE 65

7-n-Butyl-2,5-dimethyl-8-[(2,-cyano-4-biphenylyl)methyl]-1,2,4-triazolo[4,3-c]pyrimidin-3(2H)-one Formula (XII): $R_1$=n-butyl, $R_2$=methyl, X=CO, Y=N—CH$_3$, X···Y=single bond,

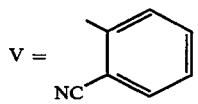

Prepared according to the procedure of Example 24. Oil used without further purification for the next step.

EXAMPLE 66

7-n-Butyl-2,5-dimethyl-8-{[2(5-tetrazolyl)-4-biphenylyl]methyl}-1,2,4-triazolo[4,3-c]pyrimidin-3 (2H)-one Formula (I): $R_1$=n-butyl, $R_2$=methyl, X=CO, Y=-N—CH$_3$, X···Y=single bond,

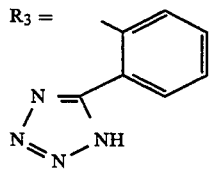

Prepared according to the procedure of Example 19. Crystals of melting point 192°–193° C.

EXAMPLE 67

6-n-Propyl-2-methyl-4-hydrazino-5-{[2,-(5-tetrazolyl)-4-biphenylyl]methyl}pyrimidine Formula (IX): $R_1$=n-propyl, $R_2$=methyl

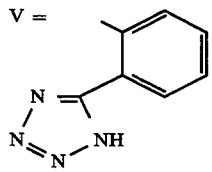

Prepared according to the procedure of Example 19, from 6-n-propyl-2-methyl-4-hydrazino-5-[(2'-cyano-4-biphenylyl)methyl]pyrimidine, prepared in Example 12. Crystals of melting point 183°–185° C.

EXAMPLE 68

7-n-Propyl-5-methyl-3-mercapto-8-{[2'-(5-tetrazolyl)-4-biphenylyl]methyl}-1,2,4-triazolo[4,3-c]pyrimidine Formula: $R_1$=n-propyl, $R_2$=methyl, X=C—SH, Y=N, X···Y=double bond,

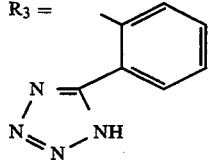

8 g of 6-n-propyl-2-methyl-4-hydrazino-5-{2'-(5-tetrazolyl)-4-biphenylyl]methyl}pyrimidine, prepared in Example 67, are dissolved in a mixture composed of 75 ml of methanol, 7 ml of water and 2.4 g of sodium hydroxide 2.5 ml of carbon disulphide are added dropwise, and the mixture is then brought to reflux for one hour and is thereafter evaporated to dryness under vacuum. The residue is taken up with 100 ml of ethanol, the mixture is heated to reflux for one hour and concentrated under vacuum and the residue is then taken up with water. On addition of acetic acid, the pH is brought to 5, and the crystals formed are drained and then chromatographed on silica gel, with ethyl acetate as eluent, to give 1.4 g of 7-n-propyl-5-methyl-3-mercapto-S-{[2'-(5-tetrazolyl)-4-biphenylyl]methyl}-1,2,4-triazolo[4,3-c]pyrimidine in the forth of crystals of melting point 247°-248° C.

EXAMPLE 69

7-n-Propyl-5-methyl-8-[(2'-cyano-4-biphenylyl)methyl]-1,2,4-triazolo[4,3-c]pyrimidine Formula (XII): $R_1$=n-propyl, $R_2$=methyl, X=CH, Y=N, X···Y=double bond,

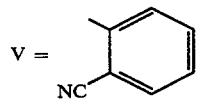

20 g of 6-n-propyl-2-methyl-4-hydrazino-5-[(2'-cyano-4-biphenylyl)methyl]pyrimidine, prepared in Example 12, are heated to reflux for 6 hours in 200 ml of triethyl orthoformate. The mixture is then concentrated under vacuum and the residue is taken up with ether. The crystals obtained are drained and washed with ether to give 18.8 g of 7-n-propyl-5-methyl-8-[(2'-cyano-4-biphenylyl)methyl]-1,2,4-triazolo[4,3-c]pyrimidine in the form of crystals of melting point 153° C.

EXAMPLE 70

7-n-Propyl-5-methyl-8-[(2'-cyano-4-biphenylyl)methyl]-1,2,4-triazolo[1,5-c]pyrimidine Formula (XII): $R_1$=n-propyl, $R_2$=methyl, X=N, Y=CH, X···Y=double bond,

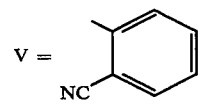

10 g of 7-n-propyl-5-methyl-8-[(2'-cyano-4-biphenylyl)methyl]-1,2,4-triazolo[4,3-c]pyrimidine, prepared in Example 69, are heated to reflux for 4 hours in 150 ml of formic acid. The mixture is evaporated to dryness under vacuum, and the residue, taken up with ether and pentane, crystallises to give 7.5 g of 7-n-propyl-5-methyl-8-[(2'-cyano-4-biphenylyl)methyl]-1,2,4-triazolo[1,5-c]pyrimidine in the form of crystals of melting point 112° C.

EXAMPLE 71

7-n-propyl-5-methyl-8-{[2'-(5-tetrazolyl)-4-biphenylyl]methyl}-1,2,4-triazolo[1,5-c]pyrimidine Formula (I): $R_1$=n-propyl, $R_2$=methyl, X=N, Y=CH, X···Y=double bond,

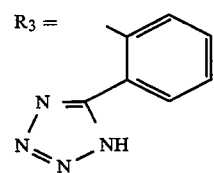

Prepared according to the procedure of Example 19. Crystals of melting point 183°-184° C.

EXAMPLE 72

7-n-propyl-5-methyl-8-{[2'-(5-tetrazolyl)-4-biphenylyl]methyl}-1,2,4-triazolo[4,3-c]pyrimidine Formula (I): $R_1$=n-propyl, $R_2$=methyl, X=CH, Y=N, X···Y=double bond,

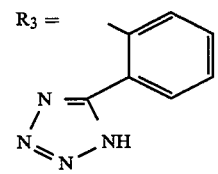

4.8 g of 6-n-propyl-2-methyl-4-hydrazino-5-{[2'(5-tetrazolyl)-4-biphenylyl]methyl}pyrimidine, prepared in Example 67, are heated to reflux for 4 hours in 40 ml of triethyl orthoformate. The mixture is evaporated under vacuum and the residue is crystallised in an ethyl acetate/isopropyl ether mixture to give 1 g of 7-n-propyl-5-methyl-8-{[2'-(5-tetrazolyl)-4biphenylyl]methyl}-1,2,4-triazolo[4,3-c]pyrimidine in the form of crystals of melting point 182°-184° C.

EXAMPLE 73

7-n-Propyl-2,5-dimethyl-8-[(2'-cyano-4-biphenylyl)methyl]-1,2,4-triazolo[1,5-c]pyrimidine Formula (XII): $R_1$—n-propyl, $R_2$=methyl, X=N, Y=C—CH$_3$, X···Y=double bond,

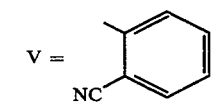

6 g of 6-n-propyl-2-methyl-4-hydrazino-5-[(2'-cyano-4-biphenylyl)methyl]pyrimidine, prepared in Example 12, are heated to 90° C. for 5 hours in 100 ml of triethyl orthoacetate. The mixture is then evaporated under vacuum and the residue is taken up in 75 ml of formic acid. The solution obtained is heated to reflux for 5 hours, the formic acid is then evaporated off under vacuum and the residue is crystallised in an ether/pentane mixture to give 5 g of 7-n-propyl-2,5-dimethyl-8-[(2'-cyano-4biphenylyl)methyl]-1,2,4-triazolo[1,5-c]pyrimidine in the form of crystals of melting point 132° C.

EXAMPLE 74

7-n-Propyl-2,5-dimethyl-8-{[2'-(5-tetrazolyl)-4-biphenylyl}methyl]-1,2,4-triazolo[1,5-c]pyrimidine Formula (I):$R_1$=n-propyl, $R_2$=methyl, X=N, Y=-C—CH$_3$, X···Y=double bond, $R_3 =$
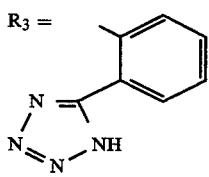

Prepared according to the procedure of Example 19. Crystals of melting point 188°–190° C.

EXAMPLE 75

7-n-Propyl-5-methyl-2-trifluoromethyl-8-[(2'-cyano-4-biphenylyl)methyl]-1,2,4-triazolo[1,5-c]pyrimidine Formula (XII): $R_1$=n-propyl, $R_2$=methyl, X=N, Y=C—CF$_3$, X···Y=double bond, $V =$
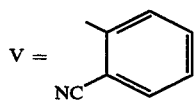

10 g of 6-n-propyl-2-methyl-4-hydrazino-S-[(2'-cyano-4-biphenylyl)methyl]pyrimidine, prepared in Example 12, are dissolved in 100 ml of anhydrous tetrahydrofuran, and 5 ml of trifluoroacetic anhydride are added dropwise. The mixture is heated to reflux for 2 hours and the solvent is evaporated off under vacuum. The residue obtained is taken up in 40 ml of phosphorus oxychloride and the solution obtained is heated to reflux for 4 hours. The phosphorus oxychloride is evaporated off under vacuum and the residue is then taken up in 40 ml of formic acid and heated to reflux for 3 hours. After evaporation of the formic acid under vacuum, the oily residue is chromatographed on silica gel in isopropyl ether to give 4.8 g of 7-n-propyl-5-methyl-2-trifluoromethyl-8-[(2'-cyano-4-biphenylyl)methyl]-1,2,4-triazolo[1,5-c]pyrimidine in the form of an oil, which is used without further purification for the next step.

EXAMPLE 76

7-n-Propyl-5-methyl-2-trifluoromethyl-8-{[2'-(5-tetrazolyl)-4-biphenylyl]methyl}-1,2,4-triazolo[1,5-c]pyrimidine Formula (I): $R_1$=n-propyl, $R_2$=methyl, X=N, Y=C—CF$_3$, X···Y=double bond, $R_3 =$
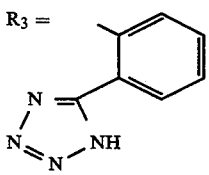

Prepared according to the procedure in Example 19. Crystals are melted at 161°–162° C.

EXAMPLE 77

7-n-Propyl-5-methyl-8-[(2'-cyano-4-biphenylyl)methyl]-2-ethyl-1,2,4-triazolo[1,5-c]pyrimidine Formula (XII): $R_1$=n-propyl, $R_2$=methyl, X=N, Y=C—C$_2$H$_5$, X···Y=double bond, $V =$
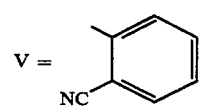

Prepared according to the procedure of Example 73, from triethyl orthopropionate.
Crystals have melting point of 96° C.

EXAMPLE 78

7-n-Propyl-5-methyl-8-{[2'(5-tetrazolyl)-4-biphenylyl]methyl}-2-ethyl-1,2,4-triazolo[1,5-c]pyrimidine Formula (I): $R_1$=n-propyl, $R_2$=methyl, X=N, Y=C—C$_2$H$_5$, X···Y=double bond, $R_3 =$
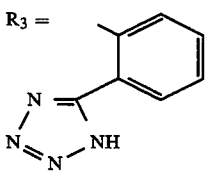

Prepared according to the procedure in Example 19. Crystals have melting point 190°–191° C.

EXAMPLE 79

7-n-Propyl-5-methyl-2-methylamino-8-[(2'-cyano-4-biphenylyl) methyl]-1,2,4-triazolo[1,5-c]pyrimidine Formula (XII): $R_1$=n-propyl, $R_2$=methyl, X=N, Y=C—NH—CH$_3$, X···Y=double bond, $V =$
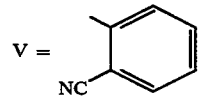

5 g of 6-n-propyl-2-methyl-5-[(2'-cyano-4-biphenylyl)methyl]-4-(4'-methyl-5-methylisothiosemicarbazido)pyrimidine hydriodide are heated to reflux for 4 hours in 50 ml of 2-ethoxyethanol in the presence of 1.5 g of potassium carbonate. The solvent is then evaporated off under vacuum and the residue is taken up with water, and the crystals formed are drained, washed with water and then with ether to give 3.3 g of 7-n-propyl-5-methyl-2-methylamino-8-[(2'-cyano-4-biphenylyl) methyl]-1,2,4-triazolo[1,5-c]pyrimidine in the form of crystals of melting point 159° C.

Preparation of 6-n-propyl-2-methyl-5- [(2 '-cyano-4-biphenylyl)methyl]-4-(4'-methyl-8-methylisothiosemicarbazido)pyrimidine hydriodide:

10 g of 6 -n-propyl-2-methyl-5- [(2 '-cyano-4-biphenylyl)methyl]-4-hydrazinopyrimidine, prepared as in Example 12, are dissolved in 100 ml of toluene. 2.1 g of methyl isothiocyanate are added, and the mixture is heated to reflux for 2 hours and then left overnight at room temperature. 2 ml of methyl iodide are added and the mixture is brought to reflux for 2 hours. After cooling, the crystals formed are drained and washed with ether to give 14 g of 6-n-propyl-2-methyl-5-[(2 '-cyano-4-biphenylyl)methyl]-4-(4'-methyl-8-methylisothiosemicarbazido)pyrimidine hydriodide in the form of crystals of melting point 220° C. (decomposition).

EXAMPLE 80

7-n-Propyl-5-methyl-2-methylamino-8-{[2'-(5-tetrazolyl)-4-biphenylyl]methyl}-1,2,4-triazolo[1,5-c]pyrimidine Formula (I): $R_1$=n-propyl, $R_2$=methyl, X=N, Y=-C—NH—CH$_3$, X$\cdots$Y=double bond,

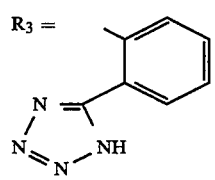

Prepared according to the procedure of Example 19.
Crystals of melting point 229°–230° C.

EXAMPLE 81

Ethyl 3-oxopentanoate

Formula (II): $R_1$=ethyl, $R_6$=ethyl
Prepared according to the procedure of Example 1.
Oil of boiling point b.p.$_{15}$=86°–90° C.

EXAMPLE 82

Ethyl 2-[(2'-cyano-4-biphenylyl)methyl]-3-oxopentanoate

Formula (IV): $R_1$=ethyl, $R_6$=ethyl

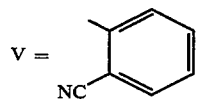

Prepared according to the procedure of Example 3.
Oil used without further purification for the next step.

EXAMPLE 83

6-Ethyl-2-methyl-5-[(2'-cyano-4-biphenylyl)methyl]-4-hydroxypyrimidine

Formula (VII): $R_1$=ethyl, $R_2$=methyl

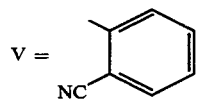

Prepared according to the procedure of Example 6.
Crystals of melting point 188° C.

EXAMPLE 84

6-Ethyl-2-methyl-5-[(2'-cyano-4-biphenylyl)methyl]-4-chloropyrimidine

Formula (VIII): $R_1$=ethyl, $R_2$=methyl

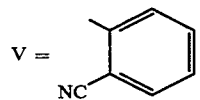

Prepared according to the procedure of Example 9.
Crystals of melting point 80° C.

EXAMPLE 85

6-Ethyl-2-methyl-4-hydrazino-5-[(2'-cyano-4-biphenylyl)methyl]pyrimidine

Formula (IX): $R_1$=ethyl, $R_2$=methyl

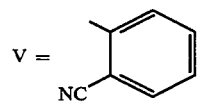

Prepared according to the procedure of Example 12.
Crystals of melting point 190° C.

EXAMPLE 86

7-Ethyl-5-methyl-8-[(2'-cyano-4-biphenylyl)methyl]-1,2,4-triazolo[4,3-c]pyrimidine Formula (XII): $R_1$=ethyl, $R_2$=methyl, X=CH, Y=N, X$\cdots$Y=double bond,

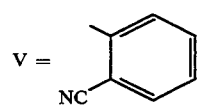

Prepared according to the procedure of Example 69.
Crystals of melting point 166° C.

EXAMPLE 87

7-Ethyl-5-methyl-8-[(2'-cyano-4-biphenylyl)methyl]-1,2,4-triazolo[1,5-c]pyrimidine Formula (XII): $R_1$=ethyl, R=2 methyl, X=N, Y=CH, X$\cdots$Y=double bond,

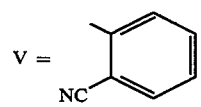

Prepared according the procedure of Example 70.
Crystals of melting point 117° C.

EXAMPLE 88

7-Ethyl-5-methyl-8-{[2'-(5-tetrazolyl)-4-biphenylyl]methyl}-1,2,4-triazolo[1,5-c]pyrimidine Formula (I): $R_1$=ethyl, R=2methyl, X=N, Y=CH, X$\cdots$Y=double bond,

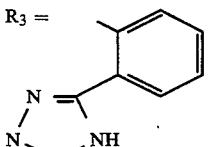

Prepared according to the procedure of Example 19.
Crystals of melting point 146°–148° C.

EXAMPLE 89

7-Ethyl-2,5-dimethyl-8-[(2'-cyano-4-biphenylyl)methyl]-1,2,4-triazolo[1,5-c]pyrimidine Formula (XII): R$_1$=ethyl, R$_2$=methyl, X=N, Y=-C—CH$_3$, X···Y=double bond, V = 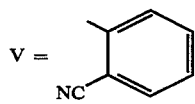

Prepared according to the procedure of Example 73. Crystals of melting point 126° C.

EXAMPLE 90

7-Ethyl-2,5-dimethyl-8-{[2'-(5-tetrazolyl)-4-biphenylyl]methyl}-i,2,4-triazolo[1,5-c]pyrimidine Formula (I): R$_1$=ethyl, R$_2$=methyl, X=N, Y=-C—CH$_3$, X···Y=double bond, R$_3$ = 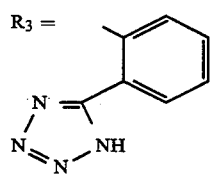

Prepared according to the procedure of Example 19. Crystals of melting point 230°–231° C.

EXAMPLE 91

2,7-Diethyl-5-methyl-8-[(2'-cyano-4-biphenylyl)methyl]-1,2,4-triazolo[1,5-c]pyrimidine Formula (XII): R$_1$=ethyl, R$_2$=methyl, X=N, Y=-C—C$_2$H$_5$. X···Y=double bond, V = 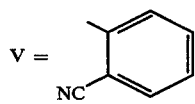

Prepared according to the procedure of Example 73, from triethyl orthopropionate.
Crystals of melting point 96° C.

EXAMPLE 92

2,7-Diethyl-5-methyl-8-{[2'-(5-tetrazolyl)-4-biphenylyl]methyl}-1,2,4-triazolo[1,5-c]pyrimidine Formula (I): R$_1$=ethyl, R$_2$methyl, X=N, Y=-C—C$_2$H$_5$. X···Y=double bond, R$_3$ = 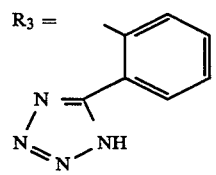

Prepared according to the procedure of Example 19. Crystals of melting point 220°–222° C.

EXAMPLE 93

7-n-Propyl-5-methyl-2-phenyl-8-[(2'-cyano-4-biphenylyl)methyl]-1,2,4-triazolo[1,5-c]pyrimidine Formula (XII): R$_1$=n-propyl, R$_2$=methyl, X=N, Y=C-phenyl, X···Y=double bond, V = 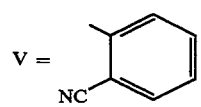

Prepared according to the procedure of Example 73, from triethyl orthobenzoate.
Oil used without further purification for the next step.

EXAMPLE 94

7-n-Propyl-5-methyl-2-phenyl-8-{[2'-(5-tetrazolyl)-4-biphenylyl]methyl}-1,2-4-triazolo[1,5-c]pyrimidine Formula (I):R$_1$=n-propyl, R$_2$=methyl, X=N, Y=C-phenyl, X···Y=double bond, R$_3$ = 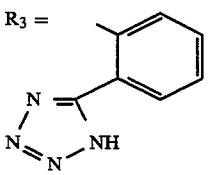

Prepared according to the procedure of Example 19. Crystals of melting point 196° C.

EXAMPLE 95

7-Ethyl-5-methyl-8-[(2'-cyano-4-biphenylyl)methyl]-1,2,4-triazolo[4,3-c]pyrimidin-3(2H)-one Formula (XII): R$_1$=ethyl, R$_2$=methyl, X=CO, Y=NH, X···Y=single bond, V = 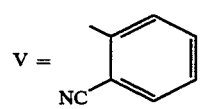

Prepared according to the procedure of Example 15. Crystals of melting point 174° C.

EXAMPLE 96

7-Ethyl-5-methyl-8-[(2'-cyano-4-biphenylyl)methyl]-1,2,4-triazolo[1,5-c]pyrimidin-2(3H)-one Formula (XII): R$_1$=ethyl, R$_2$=methyl, X=NH, Y=CO, X···Y=single bond, V = 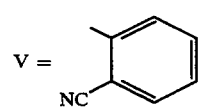

Prepared according to the procedure of Example 18. Crystals of melting point 246° C.

EXAMPLE 97

7-Ethyl-5-methyl-8-{[2'(5-tetrazolyl)-4-biphenylyl]methyl}-1,2,4-triazolo[1,5-c]pyrimidin-2(3H)-one Formula (I): R$_1$=ethyl, R$_2$=methyl, X=NH, Y=CO, X···Y=single bond,

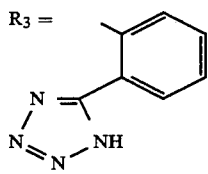

Prepared according to the procedure of Example 19. Crystals of melting point 254° C.

EXAMPLE 98

7-n-Butyl-5-methyl-2-trifluoromethyl-8-[(2'-cyano-4-biphenylyl)methyl]-1,2,4-triazolo[1,5-c]pyrimidine Formula (XII): R$_1$=n-butyl, R$_2$=methyl, X=N, Y=C—CF$_3$, X···Y=double bond,

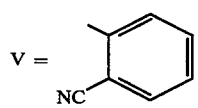

Prepared according to the procedure of Example 75. Crystals of melting point 110° C.

EXAMPLE 99

7-n-Butyl-5-methyl-2-trifluoromethyl-8-{[2'-(5-tetrazolyl)-4-biphenylyl]methyl}-1,2,4-triazolo[1,5-c]pyrimidine Formula (I): R$_1$=n-butyl, R$_2$=methyl, X=N, Y=C—CF$_3$, X···Y=double bond,

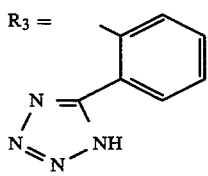

Prepared according to the procedure of Example 19. Crystals of melting point 179°–180° C.

EXAMPLE 100

6-n-Propyl-2-mercapto-4-hydroxy-5-[(2'-cyano-4-biphenylyl)methyl]pyrimidine

Formula (VII): R$_1$=n-propyl, R$_2$=SH,

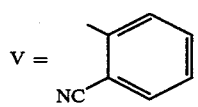

5.7 g of sodium are dissolved in 150 ml of methanol, and 19 g of thiourea are added to this solution. The mixture is stirred for 5 minutes and 58 g of ethyl 3-oxo-2-[(2'-cyano-4-biphenylyl)methyl]hexanoate, prepared in Example 4, are added. The mixture is then heated to reflux for 10 hours and the methanol is evaporated off under vacuum. The residue is taken up with water and washed with ether, the aqueous phase is neutralised by adding dilute hydrochloric acid and the crystals obtained are filtered off and washed with water and with ether to give 26 g of 6-n-propyl-2-mercapto-4-hydroxy-5-[(2'-cyano-4-biphenylyl)methyl]pyrimidine in the form of crystals of melting point 191° C.

EXAMPLE 101

6-n-Propyl-2-methylthio-4-hydroxy-5-[(2'-cyano-4-biphenylyl)methyl]pyrimidine

Formula (VII): R$_1$=n-propyl, R$_2$=SCH$_3$,

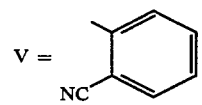

26 g of 6-n-propyl-2-mercapto-4-hydroxy-5[(2'-cyano-4-biphenylyl)methyl]pyrimidine, prepared in Example 100, are stirred for 15 minutes in a solution of 5 g of potassium hydroxide in 100 ml of methanol. 6 ml of methyl iodide are added to the mixture, which is then stirred for 4 hours at room temperature. The crystals formed are drained, washed with water and then with ether and dried to give 23 g of 6-n-propyl-2-methylthio-4-hydroxy-5-[(2'-cyano-4-biphenylyl)methyl]pyrimidine in the form of crystals of melting point 218° C.

EXAMPLE 102

6-n-Propyl-2-methylthio-4-chloro-5-[(2'-cyano-4-biphenylyl)methyl]pyrimidine

Formula (VIII): R$_1$=n-propyl, R$_2$=SCH$_3$,

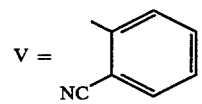

Prepared according to the procedure of Example 9. Crystals of melting point 88° C.

EXAMPLE 103

6-n-Propyl-2-methylthio-4-hydrazino-5-[(2'-cyano-4-biphenylyl)methyl]pyrimidine

Formula (IX): R$_1$=n-propyl, R$_2$=SCH$_3$,

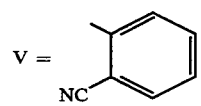

Prepared according to the procedure of Example 12. Crystals of melting point 106° C.

EXAMPLE 104

6-n-Propyl-2-methylthio-4-hydrazino-5-{[2'-(5-tetrazolyl)-4-biphenylyl]methyl}pyrimidine Formula (IX): R$_1$=n-propyl, R$_2$=SCH$_3$, V = 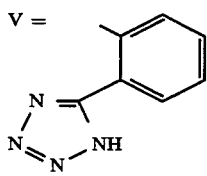

Prepared according to the procedure of Example 19. Crystals of melting point 224° C.

EXAMPLE 105

7-n-Propyl-5-methylthio-8-{[2'-(5-tetrazolyl)-4-biphenylyl]methyl}-1,2,4-triazolo[-4,3-c]pyrimidin-3 (2H)-one Formula (I): $R_1$=n-propyl, $R_2$=$SCH_3$, X=CO, Y=NH, X···Y=single bond, $R_3$ = 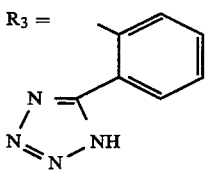

Prepared according to the procedure of Example 15, chromatographed on silica gel ($CHCl_3$/MeOH,9:1). Crystals of melting point 259°–261° C.

EXAMPLE 106

7-n-Propyl-5-methyl-2-amino-8-[(2'-cyano-4-biphenylyl)methyl]-1,2,4-triazolo[1,5-c]pyrimidine Formula (XII): $R_1$=n-propyl, $R_2$=methyl, X=N, Y=C—$NH_2$, X···Y=double bond, V = 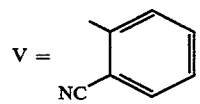

10 g of 6-n-propyl-2-methyl-4-hydrazino-5-[(2'-cyano-4-biphenylyl)methyl]pyrimidine, prepared in Example 12, and 5 g of 2-methyl-2-thiopseudourea sulphate are heated to reflux for 16 hours. After the addition of water, the crystals formed are drained and washed with ether and then with ethyl acetate before taken up in dilute sodium hydroxide solution and extracted with chloroform. The organic phase is dried over magnesium sulphate and evaporated under vacuum, to give a residue which crystallises in a mixture of isopropyl ether and ethyl acetate to give 1.8 g of 7-n-propyl-5-methyl-2-amino-8-[(2'-cyano-4-biphenylyl)methyl]-1,2,4-triazolo[1,5-c]pyrimidine in the form of crystals of melting point 150° C.

EXAMPLE 107

7-n-Propyl-5-methyl-2-amino-8-{[2'-(5-tetrazolyl)-4-biphenylyl]methyl}-1,2,4-triazolo[1,5-c]pyrimidine Formula (I): $R_1$=n-propyl, $R_2$=methyl, X=N Y=C—$NH_2$, X···Y=double bond, $R_3$ = 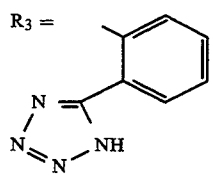

Prepared according to the procedure of Example 19. Crystals of melting point 170°–174° C.

EXAMPLE 108

Ethyl 7-n-propyl-5-methyl-8-[(2'-cyano-4-biphenylyl)methyl]-1,2,4-triazolo[1,5-c]pyrimidine-2-carboxylate Formula (XII): $R_1$=n-propyl, $R_2$=methyl, X=N, Y=C—$CO_2Et$, X···Y=double bond, V = 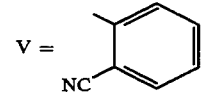

34.6 g of 6,n-propyl-2-methyl-4-hydrazino-5-[(2'-cyano-4-biphenylyl)methyl]pyrimidine, prepared in Example 12, are dissolved in 500 ml of chloroform stabilised with amylene in the presence of 13.9 g of triethylamine. 13.2 ml of ethoxalyl chloride are added dropwise, and the mixture is stirred for 1 hour at room temperature and then 2 hours under reflux. After washing with water, the chloroform phase is dried and evaporated under vacuum, and the residue, which crystallises in an acetate/ether mixture, gives 25 g of hydrazide of melting point 176° C. This hydrazide is then heated to reflux for 6 hours in 60 ml of phosphorus oxychloride. The mixture is concentrated under vacuum, the residue is then taken up with chloroform and the solution obtained is washed with water and with sodium bicarbonate solution before being dried over magnesium sulphate and evaporated under vacuum. The residue obtained crystallises in an ether/isopropyl ether mixture to give 15.7 g of ethyl 7-n-propyl-5-methyl-8-[(2'-cyano-4-biphenylyl)methyl]-1,2,4-triazolo[1,5-c]pyrimidine-2-carboxylate in the form of crystals of melting point 108° C.

EXAMPLE 109

Ethyl 7-n-propyl-5-methyl-8-{[2'-(5-tetrazolyl)-4-biphenylyl]-methyl}-1,2,4-triazolo[1,5-c]pyrimidine-2-carboxylate Formula (I): $R_1$=n-propyl, $R_2$=methyl, X=N, Y=C—$CO_2Et$, X···Y=double bond, $R_3$ = 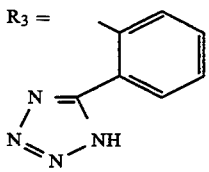

Prepared according to the procedure of Example 19. Crystals of melting point 168°–170° C.

EXAMPLE 110

7-n-Propyl-5-methyl-8-{[2'-(5-tetrazolyl)-4-biphenylyl]-methyl}-1,2,4-triazolo[1,5-c]pyrimidine-2-carboxylic acid Formula (I): $R_1$=n-propyl, $R_2$=methyl, X=N, Y=-C—$CO_3H$, X···Y=double bond,

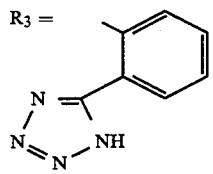

2.8 g of ethyl ? -propyl-5-methyl- 2'- 5-tetrozyl)-biphenylyl]methyl>-2-triazolo[,1,5-c]pyrimidine-2-carboxylate, prepared in Example 109, are dissolved in a solution of 1.8 g of sodium carbonate in 30 ml of water. The solution is stirred for 30 hours at room temperature, then acidified by bubbling in sulphur dioxide and extracted with dichloromethane. The organic phase is dried over magnesium sulphate and evaporated to dryness under vacuum. The residue crystallises in an acetone/ether nitrate to give 2.3 g of ? -n-propyl-5-methyl-8-{[2'-(5-tetrazolyl)-4-biphenyl]methyl}-1,2,4-triazolo[1,5-c]pyrimidine-2-carboxylic acid in the form of crystals of melting point 193°–194° C.

EXAMPLE 111

7-n-Butyl-5-methyl-8-[(2'-cyano-4-biphenylyl)methyl]-1,2,4-triazolo[1,5-c]pyrimidin-2(3H)-one Formula (XII): $R_1$=n-butyl, $R_2$=methyl, X=NH, Y=CO, X···Y=single bond,

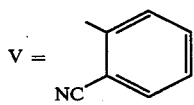

Prepared according to the procedure of Example 18. Crystals of melting point 235° C.

EXAMPLE 112

7-n-Butyl-5-methyl-8-{[2'(5-tetrazolyl)-4-biphenylyl]-methyl}-1,2,4-triazolo[1,5-c]pyrimidin-2(3H)-one Formula (I): $R_1$=n-butyl, $R_2$=methyl, X=NH, Y=CO, X···Y=single bond,

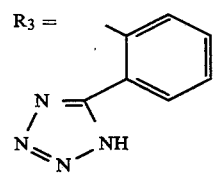

Prepared according to the procedure of Example 19. Crystals of melting point 236°–238° C.

EXAMPLE 113

4'-[(7-n-Butyl-5-methyl-2-oxo-2,3-dihydro-1,2,4-triazolo[1,5-c]pyrimidin-8-yl)methyl]-2-biphenylcarboxylic acid Formula (I): $R_1$=n-butyl, $R_2$=methyl, X=NH, Y=CO, X···Y=single bond,

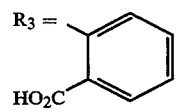

8 g of 7-n-butyl-5-methyl-8-[(2'-cyano-4-biphenylyl)-methyl]-1,2,4-triazolo[1,5-c]pyrimidin-2(3H)-one, prepared in Example 111, are heated to reflux for 10 hours in a solution of 6 g of sodium hydroxide in 30 ml of ethylene glycol and 2 ml of water. This solution, after cooling is acidified with hydrochloric acid to pH 5, and the crystals formed are drained and dried and then washed with acetone to give 5 g of 4'-[(7-n-Butyl-5-methyl-2-oxo-2,3-dihydro-1,2,4-triazolo[1,5-c]pyrimidin-8-yl}methyl]-2-biphenylcarboxylic acid in the form of crystals of melting point 210°–211° C.

EXAMPLE 114

6-n-Propyl-4-hydroxy-5-[(2'-cyano-4-biphenylyl)methyl]pyrimidine

Formula (VII): $R_1$=n-propyl, $R_2$=H

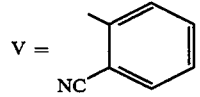

29 g of 6-n-propyl-2-methylthio-4-hydroxy-5-[(2'-cyano-4-biphenylyl)methyl]pyrimidine, prepared in Example 101, are dissolved in 250 ml of diglyme, and 60 g of Raney nickel are added. The mixture is heated to reflux for 3 hours. The catalyst is filtered off and washed with ethanol, the filtrate is evaporated under vacuum and the residue is chromatographed on silica gel in a 2:8 acetone/chloroform eluent to give 14.2 g of 6-n-propyl-4-hydroxy-5-[(2'-cyano-4-biphenylyl)methyl]pyrimidine in the form of crystals of melting point 158° C.

EXAMPLE 115

6-n-Propyl-4-chloro-5-[(2'-cyano-4-biphenylyl)methyl]-pyrimidine

Formula (VIII): $R_1$=n-propyl, $R_2$=H,

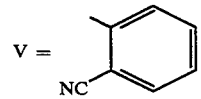

Prepared according to the procedure of Example 9. Crystals of melting point 95° C.

EXAMPLE 116

6-n-Propyl-4-hydrazino-5-[(2'-cyano-4-biphenylyl)methyl]pyrimidine

Formula (IX): $R_1$=n-propyl, $R_2$=H,

V = 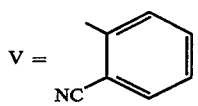

Prepared according to the procedure of Example 12.
Crystals of melting point 120° C.

EXAMPLE 117

7-n-Propyl-8-[(2'-cyano-4-biphenylyl)methyl]-1,2,4-triazolo[4,3-c]pyrimidin-3 (2H)-one Formula (XII): $R_1$=n-propyl, $R_2$=H, X=CO, Y=NH, X···Y=single bond, V = 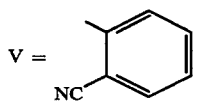

Prepared according to the procedure of Example 15.
Crystals of melting point 124° C.

EXAMPLE 118

7-n-Propyl-8-[(2'-cyano-4-biphenylyl)methyl]-1,2,4-triazolo[1,5-c]pyrimidin-2 (3H)-one Formula (XII): $R_1$=n-propyl, $R_2$=H, X=NH, Y=CO, X···Y=single bond, V = 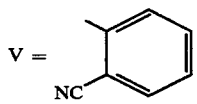

Prepared according to the procedure of Example 18.
Crystals of melting point 199° C.

EXAMPLE 119

7-n-Propyl-8-{[2-(5-tetrazolyl)-4-biphenylyl]methyl}-1,2,4-triazolo[1,5-c]pyrimidin-2 (3H)-one Formula (I): $R_1$=n-propyl, $R_2$=H, X=NH, Y=CO, X···Y=single bond, $R_3$ = 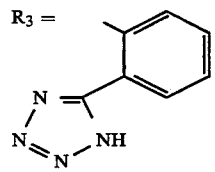

Prepared according to the procedure of Example 19.
Crystals of melting point 190°–192° C.

EXAMPLE 120

7-n-Propyl-8-[(2'-cyano-4-biphenylyl)methyl]-1,2,4-triazolo[1,5-c]pyrimidine

Formula (XII): $R_1$=n-propyl, $R_2$=H, X=N, Y=CH, X···Y=double bond,

V = 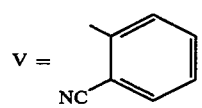

Prepared according to the procedures of Examples 69 and 70.
Crystals of melting point 104° C.

EXAMPLE 121

7-n-Propyl-8-{[2'-(5-tetrazolyl)-4-biphenylyl]methyl}-1,2,4-triazolo[1,5-c]pyrimidine Formula (I): $R_1$=n-propyl, $R_2$=H, X=N, Y=CH, X···Y=double bond, $R_3$ = 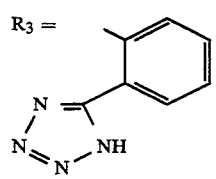

Prepared according to the procedure of Example 19.
Crystal of melting point 131°–133° C.

EXAMPLE 122

6-n-Butyl-2-methyl-4-hydrazino-5-{[2'-(5-tetrazolyl)-4-biphenylyl]methyl}pyrimidine Formula (IX): $R_1$=n-butyl, $R_2$=methyl, V = 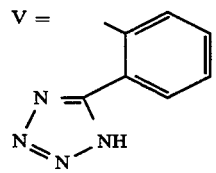

Prepared according to the procedure of Example 67.
Crystals of melting point 166° C.

EXAMPLE 123

7-n-Butyl-5-methyl-8-{[2'-(5-tetrazolyl)-5-biphenyl]methyl}-1,2,-triazolo[4,3-c]pyrimidine Formula (I): $R_1$=n-butyl, $R_2$=methyl, X=CH, Y=N, X···Y=double bond, $R_3$ = 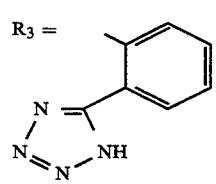

Prepared according to the procedure of Example 72, and purified by chromatography on silica gel in a 95:5 dichloromethane/methanol eluent (2nd product eluted).
Crystals of melting point 185°–186° C.

EXAMPLE 124

7-n-Butyl-5-methyl-8-{[2'-(5-tetrazolyl)-4-biphenylyl]-methyl}-1,2,4-triazolo[1,5-c]pyrimidine Formula (I): R$_1$=n-butyl, R$_2$=methyl, Y=CH, X=N, X···Y=double bond,

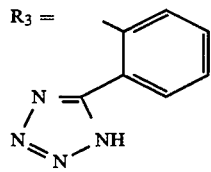

Prepared according to the procedure of Example 123, and purified by chromatography on silica gel in a 95:5 dichloromethane/methanol eluent (1st product eluted). Crystals of melting point 172°–173° C.

EXAMPLE 125

7-n-Butyl-5-methyl-8-{[2'-(5-tetrazolyl)-4-biphenylyl]-methyl}-3-mercapto-1,2,4-triazolo[4,3-c]pyrimidine
Formula (I): R$_1$=n-butyl, R$_2$=methyl, X=C—SH
Y=N X···Y=double bond,

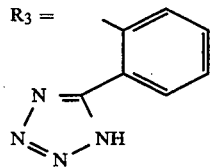

5.9 g of 6-n-butyl-2-methyl-4-hydrazino-5-{(2'-(5-tetrazolyl)-4-biphenylyl]methyl}pyrimidine, prepared in Example 122, are added to a mixture containing 3.1 ml of carbon disulphide, 1.4 g of sodium hydroxide, 36 ml of methanol and 2 ml of water. This mixture is brought to reflux for 1 hour and then evaporated to dryness; 80 ml of ethanol are added, and the mixture obtained is heated to reflux for one hour, then concentrated under vacuum, taken up with water, acidified with hydrochloric acid and extracted with dichloromethane. The organic phase is evaporated and the residue is chromatographed on silica gel in a 95:5 dichloromethane/methanol eluent to give 3.2 g of 7-n-butyl-5-methyl-8-{[2'-(5-tetrazolyl)-4-biphenylyl]methyl}-3-mercapto-1,2,4-triazolo[4,3c ]pyrimidine in the form of crystals of melting point 172°–173° C.

EXAMPLE 126

7-n-Butyl-5-methyl-8-{[2 - (5-tetrazolyl )-4-biphenylyl]methyl}-2-mercapto-1,2,4-triazolo[1,5-c]pyrimidine Formula (I): R$_1$=n-butyl, R$_2$=methyl, X=N, Y=-C—SH, X···Y =double bond,

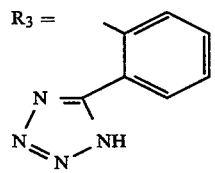

2.7 g of ? -n-butyl-S-methyl-N-8-{[2 '-(5-tetrazolyl)-4-biphenylyl ]methyl }-3-mercapto-1,2,-triazolo[4,3-c ]pyrimidine are dissolved in 100 ml of water and 0.6 g of sodium hydroxide. The mixture is heated to reflux for 3 hours, then cooled and acidified with concentrated hydrochloric acid and extracted with dichloromethane. The organic phase is dried over magnesium sulphate and evaporated under yacht. The residue is chromatographed on silica gel in a 95:5 dichloromethane/methanol eluent to give 1 g of 7-n-butyl-5-methyl-8-{[2 -(5-tetrazolyl ) -4-biphenylyl ]methyl}-2-mercapto-1,2,4-triazolo[1,5-c]pyrimidine in the forth of crystals of melting point 135°–137° C.

EXAMPLE 127

2 - [{7 -n-Butyl-5-methyl-8- [(2 '-cyano-4-biphenylyl)methyl]-1,2,4-triazolo [1,5-c]pyrimidin- 2 -yl }oxy]ethanol Formula (XII): R$_1$=n-butyl, R$_2$=methyl, X=N, Y=C—OCH$_2$—CH$_2$OH,

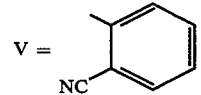

Prepared according to the procedure of Example 27, from 2-bromoethanol.

Oil used without further purification for the next step.

EXAMPLE 128

2 - [{7 -n-Butyl-5-methyl-8- [(2 '-cyano-4-biphenylyl)methyl]-1,2,4 -triazolo [1,5-c]pyrimidin-2-yl}oxy]ethyl acetate Formula (XII): R$_1$=n-butyl, R$_2$=methyl, X=N, Y=C—OCH$_2$—CH$_2$—O—CO—CH$_3$X Y=double bond,

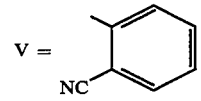

4.4 g of 2-[{7-n-Butyl-5-methyl-8-[(2'-cyano-4-biphenylyl)methyl]-1,2,4-triazolo[1,5-c]pyrimidin-2yl-}oxy]ethanol, prepared in Example 127, are heated to reflux for 2 hours in 45 ml of acetic anhydride. The mixture is then evaporated to dryness to give 5 g of 2-[{7-n-butyl-5-methyl-S-[(2'-cyano-4-biphenylyl)methyl]-1,2,4-triazolo[1,5-c]pyrimidin-2-yl}oxy]ethyl acetate in the form of an oil, which is used without further purification for the next step.

EXAMPLE 129

2-{[7-n-Butyl-5-methyl-8-{[2'-(5-tetrazolyl)-4-biphenylyl]methyl}-1,2,4-triazolo[1,5-c]pyrimidin-2-yl]oxy}ethyl acetate Formula (I): R$_1$=n-butyl, R$_2$=methyl, X=N, Y=-C—OCH$_2$—CH$_2$—O—CO—CH$_3$X Y=double bond, R3 = 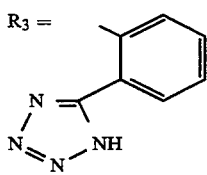

Prepared according to the procedure of Example 19.
Crystals of melting point 141°–143° C.

EXAMPLE 130

Ethyl {7-n-butyl-5-methyl-8-[(2′-cyano-4-biphenylyl)methyl]-1,2,4-triazolo[1,5-c]pyrimidin-2-yl}mercaptoacetate Formula (XII): $R_1$=n-butyl, $R_2$=methyl, X=N, Y=C—SCH$_2$—CO$_2$Et, X···Y=double bond, V = 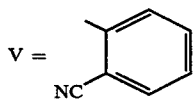

Prepared according to the procedure of Example 27, from ethyl bromoacetate and 7-n-butyl-5-methyl-2-mercapto-8-[(2′-cyano-4-biphenylyl)methyl]-1,2,4-triazolo[1,5-c]pyrimidine.

Crystals of melting point 93° C.

EXAMPLE 131

Ethyl [7-n-butyl-5-methyl-8-{[2′-(5-tetrazolyl)-4-biphenylyl]methyl}-1,2,4-triazolo[1,5-c]pyrimidin-2-yl]mercaptoacetate Formula (I): $R_1$=n-butyl, $R_2$=methyl, X=N, Y=-C—SCH$_2$-CO$_2$Et, X···Y=double bond, R3 = 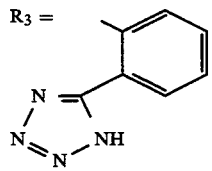

Prepared according to the procedure of Example 19.
Crystals of melting point 155°–156° C.

EXAMPLE 132

2-{[7-n-Butyl-5-methyl-8-{[2′-(5-tetrazolyl)-4-biphenylyl]methyl}-i, 2,4-triazolo[1,5-c]pyridimin-2-yl]mercapto}ethyl acetate Formula (I): $R_1$=n-butyl, $R_2$=methyl, X=N, Y=-C—SCH$_2$-CH$_2$—O—CO—CH$_3$, X···Y=double bond, R3 = 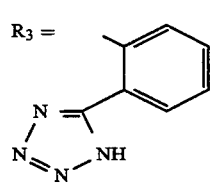

Prepared according to the procedure of Example 27, from 2-bromoethyl acetate and 7-n-butyl-5-methyl-2-mercapto-8-{[2′-(5-tetrazolyl)-4-biphenylyl]methyl}-1,2,4-triazolo[1,5-c]pyrimidine, prepared in Example 126.

Crystals of melting point 173°–175° C.

EXAMPLE 133

6-n-Propyl-2-ethyl-4-hydroxy-5-[(2′-cyano-4-biphenylyl)methyl]pyrimidine

Formula (VII): $R_1$=n-propyl, $R_2$=ethyl,

V = 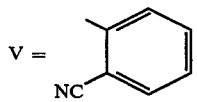

Prepared according to the procedure of Example 6.
Crystals of melting point 216° C.

EXAMPLE 134

6-n-Propyl-2-ethyl-4-chloro-5-[(2′-cyano-4-biphenylyl)methyl]pyrimidine

Formula (VIII): $R_1$=n-propyl, $R_2$=ethyl,

V = 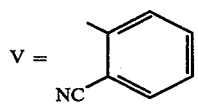

Prepared according to the procedure of Example 9.
Oil used without further purification for the next step.

EXAMPLE 135

6-n-Propyl-2-ethyl-4-hydrazino-5-[(2′-cyano-4-biphenylyl)methyl]pyrimidine

Formula (IX): $R_1$=n-propyl, $R_2$=ethyl,

V = 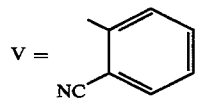

Prepared according to the procedure of Example 12.
Crystals of melting point 80° C.

EXAMPLE 136

7-n-Propyl-5-ethyl-8-[(2′-cyano-4-biphenylyl)methyl]-1,2,4-triazolo[4,3-c]pyrimidin-3(2H)-one Formula (XII): $R_1$=n-propyl, $R_2$=ethyl, X=CO, Y=NH, X···Y=single bond, V = 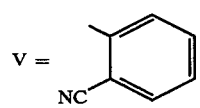

Prepared according to the procedure of Example 15.
Crystals of melting point 170° C.

EXAMPLE 137

7-n-Propyl-5-ethyl-8-[(2'-cyano-4-biphenylyl)methyl]-1,2,4-triazolo[1,5-c]pyrimidin-2 (3H)-one Formula (XII): R$_1$=n-propyl, R$_2$=ethyl, X=NH, Y=CO, X···Y=single bond,

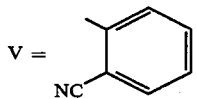

Prepared according to the procedure of Example 18. Crystals of melting point 208° C.

EXAMPLE 138

7-n-Propyl-5-ethyl-8-{[2'-(5-tetrazolyl)-4-biphenylyl]methyl}-1,2,4-triazolo[1,5-c]pyrimidin-2(3H)-one Formula (I): R$_1$=n-propyl, R$_2$=ethyl, X=NH, Y=CO, X···Y=single bond,

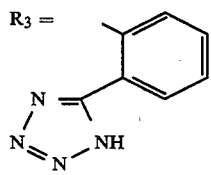

Prepared according to the procedure of Example 19. Crystals of melting point 255°–256° C.

EXAMPLE 139

2,6-Di-n-propyl-4-hydroxy-5-[(2'-cyano-4-biphenylyl)methyl]pyrimidine

Formula (VII): R$_1$=R$_2$=n-propyl,

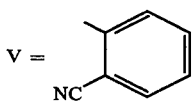

Prepared according to the procedure of Example 6. Crystals of melting point 150° C.

EXAMPLE 140

2,6-Di-n-propyl-4-chloro-5-[(2'-cyano-4-biphenylyl)methyl]pyrimidine

Formula (VIII): R$_1$=R$_2$=n-propyl,

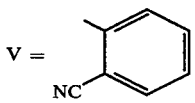

Prepared according to the procedure of Example 9. Oil used without further purification for the next step.

EXAMPLE 141

2,6-Di-n-propyl-4-hydrazino-5-[(2'-cyano-4-biphenylyl)methyl]pyrimidine

Formula (IX): R$_1$=R$_2$-n-propyl,

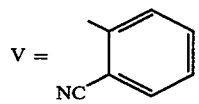

Prepared according to the procedure of Example 12. Oil used without further purification for the next step.

EXAMPLE 142

5,7-Di-n-propyl-8-[(2'-cyano-4-biphenylyl)methyl]-1,2,4-triazolo[4,3-c]pyrimidin-3(2H)-one Formula (XII): R$_1$=R$_2$=n-propyl, X=CO, Y=NH X···Y=single bond,

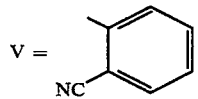

Prepared according to the procedure of Example 15. Crystals of melting point 149° C.

EXAMPLE 143

5,7-Di-n-propyl-8-[(2'-cyano-4-biphenylyl)methyl]-1,2,4-triazolo[1,5-c]pyrimidin-2 (3H)-one Formula (XII): R$_1$=R$_2$=n-propyl, X=NH, Y=CO, X···Y=single bond,

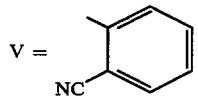

Prepared according to the procedure of Example 18. Crystals of melting point 184° C.

EXAMPLE 144

5,7-Di-n-propyl-8-{[2'-(5-tetrazolyl)-4-biphenylyl]methyl}-1,2,4-triazolo[1,5-c]pyrimidin-2(3H)-one Formula (I): R$_1$=R$_2$=n-propyl, X=NH, Y=CO, X···Y=single bond,

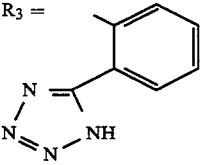

Prepared according to the procedure of Example 19. Crystals of melting point 258°–259° C.

EXAMPLE 145

Ethyl {7-n-propyl-5-methyl-8-[(2'-cyano-4-biphenylyl)methyl]-1,2,4-triazolo[1,5-c]pyrimidin-2-yl}acetate Formula (XII): R$_1$=n-propyl, R$_2$=methyl, X=N, Y=C—CH$_2$CO$_2$Et, X···Y=double bond,

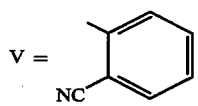

Prepared according to the procedure of Example 108, from the acid chloride of malonic acid ethyl ester.
Crystals of melting point 100° C.

EXAMPLE 146

Ethyl
[7-n-propyl-5-methyl-8-{[2'-(5-tetrazolyl)-4-biphenylyl]methyl}-1,2,4-triazolo[1,5-c]pyrimidin-2-yl]acetate Formula (I): R$_1$=n-propyl, R$_2$=methyl, X=N, Y=-C—CH$_2$CO$_2$Et, X···Y=double bond,

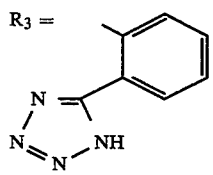

Prepared according to the procedure of Example 19.
Crystals of melting point 150° C.

EXAMPLE 147

Ethyl
{7-n-propyl-5-methyl-8-[(2'-cyano-4-biphenylyl)methyl]-1,2,4-triazolo[1,5-c]pyrimidin-2-yl}aminoacetate Formula (XII): R$_1$=n-propyl, R$_2$=methyl, X=N, Y=C—NHCH$_2$CO$_2$Et, Y=double bond,

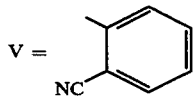

Prepared according to the procedure of Example 79, from ethyl isothiocyanatoacetate.
Crystals of melting point 132° C.

EXAMPLE 148

Ethyl
[7-n-propyl-5-methyl-8-{[2'-(5-tetrazolyl)-4-biphenylyl]methyl}-1,2,4-triazolo[1,5-c]pyrimidin-2-yl]aminoacetate Formula(I): R$_1$=n-propyl, R$_2$=methyl, X=N, Y=-C—NHCH$_2$CO$_2$Et, X···Y=double bond,

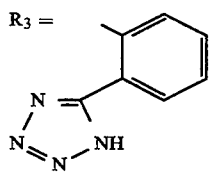

Prepared according to the procedure of Example 19.
Crystals of melting point 180°–181° C.

EXAMPLE 149

Ethyl
7-ethyl-5-methyl-8-[(2'-cyano-4-biphenyl)methyl]-1,2,4-triazolo[1,5-c]pyrimidine-2-carboxylate Formula (XII): R$_1$=ethyl, R$_2$=methyl, X=N, Y=-C—CO$_2$Et, X···Y=double bond,

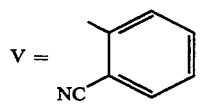

Prepared according to the procedure of Example 108.
Crystals of melting point 160° C.

EXAMPLE 150

Ethyl
7-ethyl-5-methyl-8-{[2,-(5-tetrazolyl)-4-biphenylyl]methyl}-1,2,4-triazolo[1,5-c]pyrimidine-2-carboxylate Formula (I): R$_1$=ethyl, R$_2$=methyl, X=N, Y=-C—CO$_2$Et, X···Y=double bond,

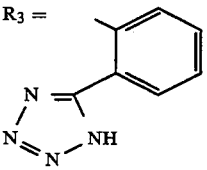

Prepared according to the procedure of Example 19.
Crystals of melting point 207°–208° C.

EXAMPLE 151

7-n-Propyl-5-methyl-2-methoxymethyl-8-[(2'-cyano-4-biphenylyl)methyl]-1,2,4-triazolo[1,5-c]pyrimidine Formula (XII): R$_1$=n-propyl, R$_2$=methyl, X=N, Y=C—CH$_2$—OCH$_3$, X···Y=double bond,

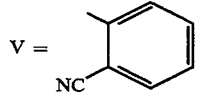

Prepared according to the procedure of Example 108, from 2-methoxyacetyl chloride.
Oil used without further purification for the next step.

EXAMPLE 152

7-n-Propyl-5-methyl-2-methoxymethyl-8-{[2'-(5-tetrazolyl)-4-biphenylyl]methyl}-1,2,4-triazolo[1,5-c]pyrimidine Formula (I): R$_1$=n-propyl, R$_2$=methyl, X=N, Y=-C—CH$_2$—OCH$_3$, X···Y=double bond,

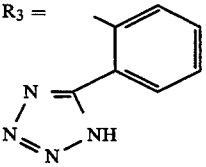

Prepared according to the procedure of Example 19.

Crystals of melting point 130°–131° C.

EXAMPLE 153

7-Ethyl-5-methyl-8-{[2'-(5-tetrazolyl)-4-biphenylyl]methyl}-1,2,4-triazolo[1,5-c]pyrimidine-2-carboxylic acid Formula (I): $R_1$=ethyl, $R_2$=methyl, X=N, Y=-C—$CO_2H$, X···Y=double bond,

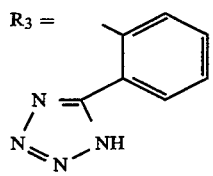

2.2 g of ethyl 7-ethyl-5-methyl-8-{[2'-(5-tetrazolyl)-4-biphenylyl]methyl}-1,2,4-triazolo[1,5c]pyrimidine-2-carboxylate, prepared in Example 150, are dissolved in 50 ml of water containing 0.56 g of sodium hydroxide. The mixture is heated to 80° C. for 3 hours, then cooled and acidified by bubbling in sulphur dioxide. The crystals formed are drained and washed with ether and with ethyl acetate to give 1.4 g of 7-ethyl-5-methyl-8-{[2'-(5-tetrazolyl)-4-biphenylyl]methyl}-1,2,4triazolo[1,5-c]pyrimidine-2-carboxylic acid in the form of crystals of melting point 194°–198° C.

EXAMPLE 154

Ethyl 3-cyclopropyl-3-oxopropionate

Formula (II): $R_1$=cyclopropyl, $R_2$=ethyl
Prepared according to the procedure of Example 1.
Oil of boiling point b.p.$_{20}$=115°–118° C.

EXAMPLE 155

Ethyl 2-[(2'-cyano-4-biphenylyl)methyl]-3-cyclopropyl-3-oxopropionate

Formula (IV): $R_1$=cyclopropyl, $R_2$=ethyl,

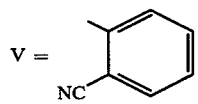

Prepared according to the procedure of Example 3.
Oil used without further purification for the next step.

EXAMPLE 156

6-Cyclopropyl-2-methyl-4-hydroxy-5-[(2'-cyano-4-biphenylyl)methyl]pyrimidine

Formula (VII): $R_1$=cyclopropyl, $R_2$=methyl,

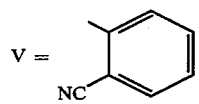

Prepared according to the procedure of Example 6.
Crystals of melting point 230° C.

EXAMPLE 157

6-Cyclopropyl-2-methyl-4-chloro-5-[(2'-cyano-4-biphenylyl)methyl]pyrimidine

Formula (VIII): $R_1$—cyclopropyl, $R_2$=methyl,

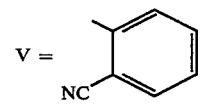

Prepared according to the procedure of Example 9.
Oil used without further purification for the next step.

EXAMPLE 158

6-Cyclopropyl-2-methyl-4-hydrazino-5-[(2'-cyano-4-biphenylyl)methyl]pyrimidine

Formula (IX): $R_1$=cyclopropyl, $R_2$=methyl,

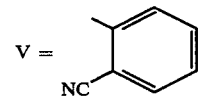

Prepared according to the procedure of Example 12.
Crystals of melting point 170° C.

EXAMPLE 159

7-Cyclopropyl-5-methyl-8-[(2'-cyano-4-biphenylyl)methyl]-1,2,4-triazolo[4,3-c]pyrimidin-3(2H)-one Formula (XII): $R_1$=cyclopropyl, $R_2$=methyl, X=CO, Y=NH, X···Y=single bond,

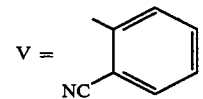

Prepared according to the procedure of Example 15.
Crystals of melting point 204° C.

EXAMPLE 160

7-Cyclopropyl-5-methyl-8-[(2'-cyano-4-biphenylyl)methyl]-1,2,4-triazolo[1,5-c]pyrimidin-2(3H)-one Formula (XII): $R_1$=cyclopropyl, $R_2$=methyl, Y=CO, X=NH, X···Y=single bond,

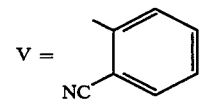

Prepared according to the procedure of Example 18.
Crystals of melting point 270° C.

EXAMPLE 161

7-Cyclopropyl-5-methyl-8-{[2'-(5-tetrazolyl)-4-biphenylyl ]methyl}-i , 2,4-triazolo[1,5-c]pyrimidin-2 (3H) -one Formula (I): $R_1$=cyclopropyl, $R_2$=methyl, Y=CO, X=NH, X···Y=single bond, R3 = 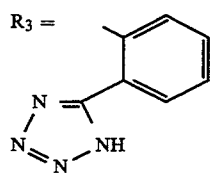

Prepared according to the procedure of Example 19. Crystals of melting point 264°–265° C.

EXAMPLE 162

7-Cyclopropyl-2,5-dimethyl-8-[(2'-cyano-4-biphenylyl)methyl]-1,2,4-triazolo[1,5-c]pyrimidine Formula (XII): $R_1$=cyclopropyl, $R_2$=methyl, Y=-C—CH3, X=N, X···Y=double bond, V = 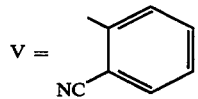

Prepared according to the procedure of Example 73. Crystals of melting point 120° C.

EXAMPLE 163

7-Cyclopropyl-2,5-dimethyl-8-{[2'-(5-tetrazolyl)-4-biphenylyl]methyl}-1,2,4-triazolo[1,5-c]pyrimidine Formula (I): $R_1$=cyclopropyl, $R_2$=methyl, Y=-C—CH3, X=N, X···Y =double bond, R3 = 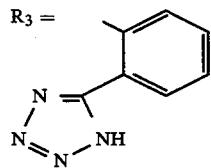

Prepared according to the procedure of Example 19. Crystals of melting point 186°–188° C.

EXAMPLE 164

6-n-Propyl-2-methoxymethyl-4-hydroxy-5-[(2'-cyano-4-biphenylyl)methyl]pyrimidine Formula (VII): $R_1$=n-propyl, $R_2$=CH2OCH3, V = 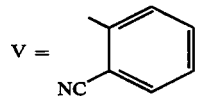

Prepared according to the procedure of Example 6, from methoxyacetamidine hydrochloride, a preparation of which may be found in the reference CA : 63, P9963e.

Crystals of melting point 134° C.

EXAMPLE 165

6-n-propyl-2-methoxymethyl-4-chloro-5-[(2,-cyano-4-biphenylyl)methyl]pyrimidine

Formula (VIII): $R_1$=n-propyl, $R_2$=CH2OCH3,

V = 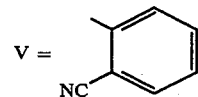

Prepared according to the procedure of Example 9. Oil used without further purification for the next step.

EXAMPLE 166

6-n-propyl-2-methoxymethyl-4-hydrazino-5-'[(2,-cyano-4-biphenylyl)methyl]pyrimidine Formula (IX): $R_1$=n-propyl, $R_2$=CH2OCH3, V = 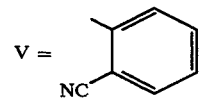

Prepared according to the procedure of Example 12. Oil used without further purification for the next step.

EXAMPLE 167

7-n-propyl-5-methoxymethyl-8-[(2'-cyano-4-biphenylyl)methyl]-1,2,4-triazolo[4,3-c]pyrimidin-3(2H)-one Formula (XII): $R_1$=n-propyl, $R_2$=CH2OCH3, X=CO, Y=NH, X···Y=single bond, V = 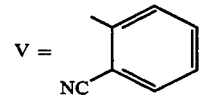

Prepared according to the procedure of Example 15. Crystals of melting point 108° C.

EXAMPLE 168

7-n-Propyl-5-methoxymethyl-8- [(2 '-cyano-4-biphenylyl ) methyl ]- 1,2,4 -triazolo [1,5-c]pyrimidin-2 (3H) -one Formula (XII): $R_1$=n-propyl, $R_2$=CH2OCH3, Y=CO, X=NH, X···Y=single bond, V = 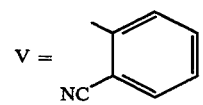

Prepared according to the procedure of Example 18. Oil used without further purification for the next step.

EXAMPLE 169

7-n-Propyl-5-methoxymethyl-8-{[2'-(5-tetrazolyl)-4-biphenylyl]methyl}-1,2,4-triazolo[1,5-c]pyrimidin-2(3H)-one Formula (I): $R_1$=n-propyl, $R_2$=CH2OCH3, Y=CO, X=NH, X···Y=single bond, $R_3 =$ 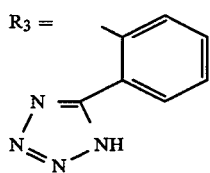

Prepared according to the procedure of Example 19. Crystals of melting point 166°–168° C.

EXAMPLE 170

7-n-Propyl-5-methoxymethyl-2-methyl-8-[(2′-cyano-4-biphenylyl)methyl]-1,2,4-triazolo[1,5-c]pyrimidine Formula (XII): $R_1$=n-propyl, $R_2$=$CH_2OCH_3$, Y=-C—$CH_3$, X=N, X···Y=double bond, $V =$ 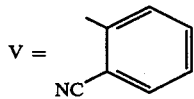

Prepared according to the procedure of Example 73. Oil used without further purification for the next step.

EXAMPLE 171

7-n-Propyl-5-methoxymethyl-2-methyl-8-{[2′-(5-tetrazolyl)-4-biphenylyl]methyl}-1,2,4-triazolo[1,5-c]pyrimidine Formula (I): $R_1$=n-propyl, $R_2$=$CH_2OCH_3$, Y=-C—$CH_3$, X=N, X···Y=double bond, $R_3 =$ 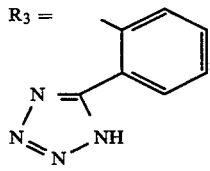

Prepared according to the procedure of Example 19. Crystals of melting point 137°–138° C.

EXAMPLE 172

4-(3-cyano-2-thienyl)benzyl bromide

A) 4′-Methyl-4-chlorobutyrophenone:

53 ml of toluene and 70.5 g of 4-chlorobutyryl chloride are dissolved in 100 ml of dichloromethane, and the solution is added at 10° C. to a suspension of 74 g of aluminium chloride in 200 ml of dichloromethane. The temperature is then allowed to rise for a quarter of an hour and the mixture is treated with ice-cold water. The organic phase is dried over magnesium sulphate and evaporated under vacuum to give 96.9 g of 4′-methyl-4-chlorobutyrophenone in the form of an oil, which is used without further purification for the next step.

B) α-Chloro-β-(2-chloroethyl)-4-methylcinnamaldehyde:

130 ml of phosphorus oxychloride are added slowly at 0° C. to 130 ml of dimethylformamide, and 117.5 g of 4′-methyl-4-chlorobutyrophenone, prepared in A), dissolved in 50 ml of dimethylformamide, are added dropwise. The mixture is then stirred at room temperature for one hour, thereafter at 50° C. for 2 hours and at 70° C. for 1 hour. The mixture is then poured onto ice and taken up with ether, and the ether phase is washed with saturated sodium bicarbonate solution, dried over sodium sulphate and evaporated under vacuum to give 133.8 g of α-chloro-β-(2-chloroethyl)-4-methylcinnamaldehyde in the form of an oil, which is used without further purification for the next step.

C) 2-(4-Methylphenyl)-4,5-dihydro-3-thiophenecarbaldehyde:

15.9 g of α-chloro-β-(2-chloroethyl)-4-methylcinnamaldehyde, prepared in B), and 22 g of sodium sulphide (9 $H_2O$) are added to 200 ml of THF. A sufficient amount of water is added for the sodium sulphide to pass completely into solution, and the mixture is then heated to reflux for 3 hours, cooled and thereafter taken up with ether. The organic phase is separated after settling has taken place, washed with water, then dried over magnesium sulphate and evaporated under vacuum to give 13.5 g of 2-(4′methylphenyl)-4,5-dihydro-3-thiophenecarbaldehyde in the form of an oil which is used without further purification for the next step.

D) 2-(4-Methylphenyl)-3-cyano-4,5-dihydrothiophene:

15 g of 2-(4-methylphenyl)-4,5-dihydro-3-thiophenecarbaldehyde, prepared in C), and 6.5 g of hydroxylamine hydrochloride are mixed in 40 ml of ethanol and 10 ml of water. A solution of 4.7 g of sodium carbonate in 10 ml of water is added. The mixture is stirred at room temperature for half an hour and then extracted with ether. The ether phase is washed with water, then dried over sodium sulphate and evaporated under vacuum to give 15.2 g of a gummy yellow residue. This residue is added to 13 ml of acetic anhydride, and the mixture becomes slightly warm, turns brown and becomes liquid. The mixture is then heated to reflux for 1 hour, thereafter poured onto ice and extracted with dichloromethane and washed with saturated sodium bicarbonate solution, the organic phase is then dried over magnesium sulphate and evaporated under vacuum, and the residue obtained is chromatographed on silica gel in dichloromethane to give 10 g of 2-(4-methylphenyl)-3-cyano-4,5-dihydrothiophene in the form of an oil, which is used without further purification for the next step.

E) 2-(4-Methylphenyl)-3-cyanothiophene:

49.9 g of 2-(4-methylphenyl)-3-cyano-4,5-dihydrothiophene, prepared in D), are dissolved in 200 ml of carbon tetrachloride, the mixture is heated to reflux and, after two hours, 11 g of bromine, dissolved in 200 ml of carbon tetrachloride, are added dropwise. Refluxing is continued until evolution of hydrobromic acid has ceased, and the solvent is evaporated off under vacuum. The residue is taken up in 200 ml of anhydrous tetrahydrofuran, and 28 g of potassium tert-butylate are added. The mixture is heated to reflux for one hour, then cooled and treated with water and sodium chloride and extracted with ether. The organic phase is evaporated under vacuum to give 31.8 g of 2-(4-methylphenyl)-3-cyanothiophene in the form of an oil, which is used without further purification for the next step.

F) 4-(3-Cyano-2-thienyl)benzyl bromide:

24.5 g of 2-(4-methylphenyl)-3-cyanothiophene, prepared in E), are dissolved in 200 ml of carbon tetrachloride. 21.9 g of N-bromosuccinimide are added, as well as 0.1 g of benzoyl peroxide. The mixture is heated to reflux for 24 hours. The crystals of succinimide are filtered off and the solvent is evaporated off under vacuum. The residue is taken up in a mixture of hexane and ethyl acetate and the solution is kept in a freezer for 24

EXAMPLE 173

Ethyl 2-[4-(3-cyano-2-thienyl)benzyl]-3-oxohexanoate

Formula (IV): $R_1$=n-propyl, $R_6$=ethyl,

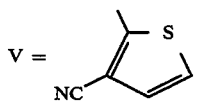

11 g of ethyl 3-oxohexanoate are dissolved in 150 ml of tetrahydrofuran. 12.9 g of 4-(3-cyano-2-thienyl)benzyl bromide and 6.1 g of lithium bromide are added and the mixture is stirred at room temperature. 24.2 ml of diisopropylethylamine are then added dropwise. After the addition is complete, the reaction mixture is brought to reflux for 24 hours. After evaporation under vacuum, the residue obtained is taken up with water and then extracted with chloroform. The organic phase is dried and then evaporated under vacuum. The excess ethyl 3-oxohexanoate is removed using a vane pump. 16.4 g of ethyl 2-[4-(3-cyano-2-thienyl)benzyl]-3-oxohexanoate are thereby obtained in the form of a pale yellow oil, which is used without further purification for the next step.

EXAMPLE 174

6-n-Propyl-2-methyl-4-hydroxy-5-[4-(3-cyano-2-thienyl)benzyl]pyrimidine

Formula (VII): $R_1$=n-propyl, $R_2$=methyl,

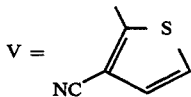

0.23 g of sodium is dissolved in 10 ml of ethanol. 1 g of acetamidine hydrochloride is added to this solution and the mixture is stirred for five minutes at room temperature. 2.4 g of ethyl 2-[4-(3-cyano-2-thienyl)benzyl]-3-oxohexanoate are then added, and the mixture is stirred for 48 hours at room temperature and then three hours under reflux. After cooling, water acidified with hydrochloric acid solution is added and a solid is allowed to deposit. This precipitate is drained, washed with water and then with a little ether and dried. 1.4 g of 6-n-propyl-2-methyl-4-hydroxy-5-[4-(3-cyano-2-thienyl)benzyl]pyrimidine are thereby recovered in the form of white crystals of melting point 180° C.

EXAMPLE 175

6-n-Propyl-2-methyl-4-chloro-5-[4-(3-cyano-2-thienyl)-benzyl]pyrimidine

Formula (VIII): $R_1$=n-propyl, $R_2$=methyl

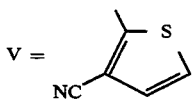

1.6 g of 6-n-propyl-2-methyl-4-hydroxy-5-[4-(3-cyano-2-thienyl)benzyl]pyrimidine are suspended in 1.7 ml of phosphorus oxychloride. The mixture is brought to reflux for 7 hours and then concentrated under vacuum. The residue obtained is dissolved in dichloromethane and then washed with aqueous sodium carbonate solution. The organic phase is then dried and thereafter evaporated. 1.8 g of 6-n-propyl-2-methyl-4-chloro-5-[4-(3-cyano-2-thienyl)benzyl]pyrimidine are thereby recovered in the form of an oil, which is used without further purification for the subsequent operations.

EXAMPLE 176

6-n-Propyl-2-methyl-4-hydrazino-5- [4- (3-cyano-2-thienyl ) benzyl ]pyrimidine

Formula (IX): $R_1$=n-propyl, $R_2$=methyl

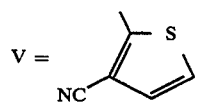

Prepared according to the procedure of Example 12. Oil used without further purification for the next step.

EXAMPLE 177

7 -n-Propyl-5-methyl-8- [4- (3-cyano-2-thienyl)benzyl]-1,2,4 -triazolo [4,3-c]pyrimidin-3 (2H) -one Formula (XII): $R_1$=n-propyl, $R_2$=methyl, X=CO, Y=NH, X⋯Y=single bond,

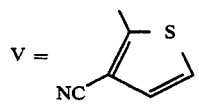

Prepared according to the procedure of Example 19. Crystals of melting point 170° C.

EXAMPLE 178

7-n-Propyl-5-methyl-8-{4- [3- (5-tetrazolyl)-2-thienyl ]benzyl}-I , 2,4-triazolo [4 , 3-c ]pyrimidin-3 (2H ) -one Formula (I): $R_1$=n-propyl, $R_2$=methyl, X=CO, Y=NH, X⋯Y=single bond,

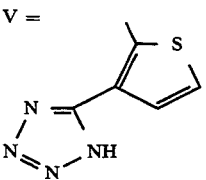

Prepared according to the procedure of Example 19. Crystals of melting point 240°–242° C.

EXAMPLE 179

7-n-Propyl-5-methyl-2- (4-pyridyl ) -8- [(2 '-cyano-4 -biphenylyl ) methyl ]- 1,2,4 -triazolo[1,5-c ]pyrimidine Formula (XII): $R_1$=n-propyl, $R_2$=methyl, X=N,

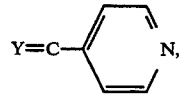

X···Y=double bond,

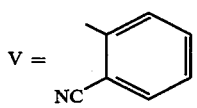

Prepared according to the procedure of Example 108, from 4-pyridinecarbonyl chloride.

Crystals of melting point 166° C.

EXAMPLE 180

7-n-Propyl-5-hydroxymethyl-8-{[2 '-(5-tetrazolyl)-4-biphenylyl ]methyl}-i, 2,4-triazolo[1,5-c ]pyrimidin-2 (3H ) -one Formula (I): $R_1$=n-propyl, $R_2$=CH$_2$OH, Y=CO, X=NH, X···Y=single bond,

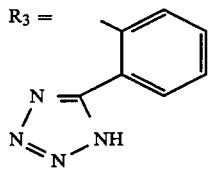

1 g of 7-n-propyl-5-methoxyethyl-8-{[2 '- (5-tetrazolyl)-4-biphenylyl]methyl}-1,2,4-triazolo[1,5-c]pyrimidin-2 (3H) -one, prepared in Example 169, are dissolved in 50 ml of chloroform stabilised with amylene. 0.7 ml of boron tribromide is added and the mixture is stirred for 8 hours at room temperature; the derivative 7-n-propyl-5-bromomethyl-8-{[2 '- (5-tetrazolyl ) -4-biphenylyl]methyl}-1,2,4-triazolo[1,5-c]pyrimidin-2(3H )-one thereby formed is taken up with dilute sodium hydroxide solution and stirred again for 6 hours. The aqueous phase is then separated after settling has taken place and acidified by bubbling in sulphur dioxide, and the crystals formed are drained, washed with acetone and then dried to give 0.6 g of 7-n-Propyl-5-hydroxymethyl-8-{[2'-(5 -tetrazolyl ) - 4 -biphenylyl ]methyl }- 1,2,4 -triazolo [1,5-c]pyrimidin-2(3H)-one in the form of crystals of melting point 182°-183° C.

EXAMPLE 181

7-n-Propyl-5-hydroxymethyl-2-methyl-8-{[2 '- (5-tetrazolyl ) -4-biphenylyl ]methyl}-1,2,4-triazolo[1,5-c ]pyrmidine Formula (I): $R_1$=n-propyl, $R_2$=CH$_2$OH, Y=C—CH$_3$, X=N, X···Y=double bond,

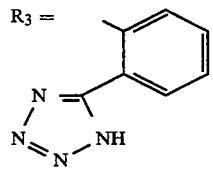

Prepared according to the procedure of Example 180, from 7-n-propyl-5-methoxymethyl-2-methyl-8-{[2'-(5-tetrazolyl)- 4-biphenylyl]methyl}-1,2,4-triazolo[1,5-c]pyrimidine prepared in Example 171.

Crystals of melting point 190°-191° C.

EXAMPLE 182

7-n-Propyl-2-hydroxymethyl-5-methyl-8-{[2'-(5-tetrazolyl)-4-biphenylyl]methyl}-1,2,4-triazolo[1,5-c]pyrimidine Formula (I): $R_1$=n-propyl, $R_2$=CH$_3$, Y=C—CH$_2$—OH, X=N, X···Y=double bond,

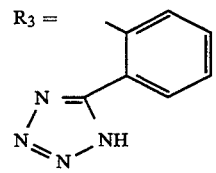

Prepared according to the procedure of Example 180, from 7-n-propyl-2-methoxymethyl-5-methyl-8-{[2'-(5-tetrazolyl)-4-biphenylyl]methyl}-1,2,4-triazolo[1,5-c]pyrimidine prepared in Example 152.

Crystals of melting point 226°-227° C.

EXAMPLE 183

Ethyl 2-{[2'-(4,4-dimethyl-2-oxazolinyl)-4-biphenylyl]methyl}-3-oxohexanoate

Formula (IV): $R_1$=n-propyl, $R_6$=ethyl,

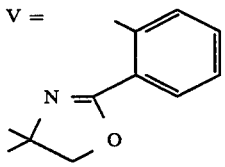

Prepared according to the procedure of Example 3, from 4'-bromomethyl-2-(4,4-dimethyl-2-oxazolinyl)-biphenyl hydrochloride, using a further equivalent of N,N,N-diisopropylethylamine in order to liberate the hydrochloride in situ.

Oil, chromatographed on silica gel in the eluent 70:30 chloroform/pentane and used without further purification for the next step.

Preparation of 4'-bromomethyl-2-(4,4-dimethyl-2-oxazolinyl)biphenyl hydrochloride:

A/ 4-(Methoxymethyl)bromobenzene:

100 g of 4-bromobenzyl bromide are dissolved in 250 ml of methanol. A solution of sodium methylate, obtained by dissolving 10 g of sodium in 500 ml of methanol, is added, and the mixture is stirred for 3 hours at room temperature. The methanol is evaporated off and the residue is taken up with ether and washed with water, the ether phase is dried over magnesium sulphate and evaporated to dryness and the residue is distilled under vacuum to give 74.3 g og 4-(methoxymethyl)-bromobenzene in the form of an oil of boiling point b.p.z0=112°-114° C.

B/ 4'-Methoxymethyl-2-(4,4-dimethyl-2-oxazolinyl)-biphenyl hydrochloride:

7.5 g of magnesium turnings are suspended in 15 ml of anhydrous tetrahydrofuran. A solution of 49 g of 4-(methoxymethyl)bromobenzene, prepared in A), in 50 ml of anhydrous tetrahydrofuran is added dropwise so as to maintain the temperature below 40° C. When all the magnesium has disappeared, a solution of 28 g of 2-(4,4-dimethyl-2-oxazolinyl)methoxybenzene, prepared according to the reference MEYERS A. I. and MIHELICH E. D.; J. AM. CHEM. SOC., 1975, 97 (25), 7383, in 100 ml of anhydrous tetrahydrofuran is added dropwise while the temperature is maintained below 50° C. The mixture is then stirred for 2 hours at room temperature and left for 48 hours. The solvent is then concentrated to one half under vacuum, the residue is poured into 1.5 l of saturated ammonium chloride solution, extracted with ether and washed with water, and the organic phase is dried over magnesium sulphate and then acidified by adding ethereal hydrogen chloride. The gummy orange precipitate which forms is separated after settling has taken place, then taken up with water and crystallised, and the crystals are washed with water and then with ether to give 26 g of 4'-methoxymethyl-2-(4,4-dimethyl-oxazolinyl)biphenyl hydrochloride in the form of crystals of melting point 108°–110° C.

C/ 4'-Bromomethyl-2-(4,4-dimethyl-2-oxazolinyl)-biphenyl hydrochloride:

5 g of 4'-methoxymethyl-2-(4,4-dimethyl-2-oxazolinyl)biphenyl hydrochloride, prepared in B/, are dissolved in 75 ml of chloroform stabilised with amylene, and 3.2 ml of boron tribromide are added while cooling to 0° C. The mixture is stirred for one hour at 0° C. and washed with cold water. The organic phase is separated after settling has taken place, then dried over magnesium sulphate and evaporated under vacuum to give 5.2 g of 4'-bromomethyl-2-(4,4-dimethyl-2-oxazolinyl)biphenyl hydrochloride in the form of crystals of melting point 126°–127° C.

EXAMPLE 184

6-n-Propyl-2-methyl-4-hydroxy-5-{[2'-(4,4-dimethyl-2-oxazolinyl)-4-biphenylyl]methyl}pyrimidine Formula (VII): $R_1$=n-propyl, $R_2$=methyl, V =
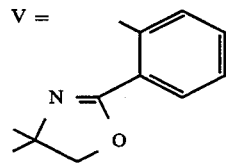

Prepared according to the procedure of Example 6. Crystals of melting point 126° C.

EXAMPLE 185

6-n-propyl-2-methyl-4-chloro-5-{[2'-(4,4-dimethyl-2-oxazolinyl)-4-biphenylyl]methyl}pyrimidine Formula (VIII): $R_1$=n-propyl, $R_2$=methyl, V =
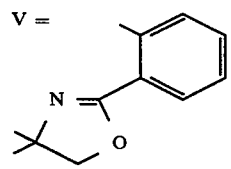

1.5 g of 6-n-propyl-2-methyl-4-hydroxy-5-{[2'-(4,4-dimethyl-2-oxazolinyl)-4-biphenylyl]methyl}pyrimidine, prepared in Example 184, are dissolved in 3 ml of thionyl chloride. 0.1 ml of dimethylformamide is added and the mixture is stirred for 1 hour at room temperature. The thionyl chloride is evaporated off under vacuum without heating, and the residue is washed with ether, then alkalinised with ammonium hydroxide solution and washed with water. The ether phase is evaporated under vacuum to give 0.6 g of 6-n-propyl-2-methyl-4-chloro-5-{[2'-(4,4-dimethyl-2-oxazolinyl)-4-biphenylyl]methyl}pyrimidine in the form of an oil, which is used without further purification for the next step.

EXAMPLE 186

6-n-Propyl-2-methyl-4-hydrazino-5-{[2'-(4, 4-dimethyl-2-oxazolinyl)-4-biphenylyl]methyl}pyrimidine Formula (IX): $R_1$=n-propyl, $R_2$=methyl, V =
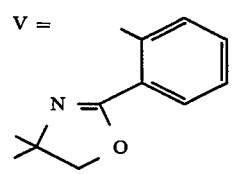

Prepared according to the procedure of Example 12. Oil used without further purification for the next step.

EXAMPLE 187:

7-n-Propyl-2,5-dimethyl-8-{[2'-(4,4-dimethyl-2,-oxazolinyl)-4-biphenylyl]methyl}- 1,2,4-triazolo[1,5-c]pyrimidine Formula (I): $R_1$=n-propyl, $R_2$=methyl, X=N, Y=-C—CH$_3$, X$\cdots$Y =double bond, $R_3$ =
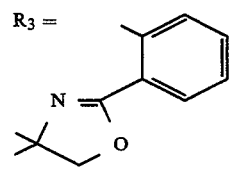

Prepared according to the procedure of Example 73. Crystals of melting point 135°–136° C.

EXAMPLE 188

7-n-Propyl-2,5-dimethyl-8-[(2'-cyano-4-biphenylyl)methyl]-1,2,4-triazolo[1,5-c]pyrimidine Formula (XII): $R_1$=n-propyl, $R_2$=methyl, X=N, Y=C—CH$_3$, X$\cdots$Y=double bond, V =
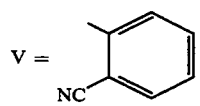

10 g of 7-n-propyl-2,5-dimethyl-8-{[2'-(4,4-dimethyl-2'-oxazolinyl)-4-biphenylyl]methyl}- 1,2,4-triazolo[1,5-c]pyrimidine, prepared in Example 187, are dissolved in 50 ml of pyridine, and 10 ml of phosphorus oxychloride are added dropwise while the temperature is maintained below 15° C. The mixture is then heated to 100° C. for 3 h and thereafter evaporated under vacuum, and the residue is cast into an ice/water mixture and extracted with chloroform. The organic phase is dried over magnesium sulphate and evaporated under vacuum to give 6 g of 7-n-Propyl-2,5-dimethyl-8-[(2'- cyano-4-biphenylyl)methyl]-1,2,4-triazolo[1,5-c]pyrimidine in the form of crystals of melting point 132° C. This compound is identical to that of Example 73.

EXAMPLE 189

6-n-Propyl-2-methyl-4-hydroxypyrimidine

Formula (XIII): $R_1$=n-propyl, $R_2$=$CH_3$

Prepared according to the procedure of Example 6, using ethyl butyrylacetate and acetamidine hydrochloride in ethanol in the presence of sodium ethylate.

Crystals of melting point: 95° C.

EXAMPLE 190

6-n-Propyl-2-methyl-4-chloropyrimidine

Prepared according to the procedure of Example 9. Crystals of melting point: 55° C.

EXAMPLE 191

6-n-Propyl-2-methyl-4-hydrazinopyrimidine

Prepared according to the procedure of Example 12. Crystals of melting point: 101° C.

EXAMPLE 192

7-n-Propyl-5-methyl-1,2,4-triazolo[4,3-c]pyrimidin-3(2H)-one

Formula (XVII): $R_1$=n-propyl, $R_2$=$CH_3$, Y=NH, X=CO, X⋯Y=single bond,

Prepared according to the procedure of Example 15. Crystals of melting point: 145° C.

EXAMPLE 193

7-n-Propyl-5-methyl-1,2,4-triazolo[1,5-c]pyrimidin-2(3H)-one

Formula (XVII): $R_1$=n-propyl, $R_2$=$CH_3$, Y=C=O, X=NH, X⋯Y=single bond,

A solution of 15.5 g of 7-n-propyl-5-methyl-1,2,4-triazolo[4,3-c]pyrimidin-3(2H)-one, prepared in Example 192, in 100 ml of acetic acid is heated to reflux for 20 h. The reaction mixture is then evaporated under vacuum, and the residue obtained crystallises in ethyl ether. The drained crystals are washed with ethyl ether and dried. 12 g of 7-n-propyl-5-methyl-1,2,4-triazolo[1,5-c]pyrimidin-2(3H)-one are obtained in the form of crystals of melting point 173° C.

EXAMPLE 194

7-n-Propyl-5-methyl-8-bromo-1,2,4-triazolo[1,5-c]pyrimidin-2(3H)-one

Formula (XVI): $R_1$=n-propyl, $R_2$=$CH_3$, Y=C=O, X=NH, X⋯Y =single bond,

A solution of 10 g of 7-n-propyl-5-methyl-1,2,4-triazolo[1,5-c]pyrimidin-2(3H)-one, prepared in Example 193, in 120 ml of acetic acid containing 12 g of sodium acetate, and to which a solution of 2.6 ml of bromine in 50 ml of acetic acid has been added dropwise, is stirred at room temperature for 3 hours. The reaction mixture is then concentrated under vacuum and thereafter treated with water. The crystals formed are drained, washed with water and dried. 7 g of 7-n-propyl-5-methyl-8-bromo-1,2,4-triazolo[1,5-c]pyrimidin-2(3H)-one are thereby obtained in the form of crystals of melting point 221° C.

EXAMPLE 195

7-n-Propyl-5-methyl-8-[(2'-cyano-4-biphenylyl)methyl]-1,2,4-triazolo[1,5-c]pyrimidin-2(3H)-one Formula (XII): $R_1$=n-propyl, $R_2$=$CH_3$, Y=C=O, X=NH, X⋯Y=single bond,

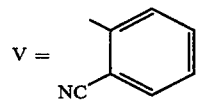

7.5 g of activated zinc powder are added at room temperature to a solution of 14 g of 4'-bromomethyl-2-cyanobiphenyl in 60 ml of anhydrous tetrahydrofuran. The mixture is stirred at room temperature for 4 h. A solution of 7 g of 7-n-propyl-5-methyl-8-bromo-1,2,4-triazolo[1,5-c]pyrimidin-2(3H)-one, prepared in Example 194, in 40 ml of anhydrous tetrahydrofuran is then added to the reaction mixture, and a solution of 527 mg of tris(dibenzylideneacetone)dipalladium(0) and 1032 g of tri-o-tolylphosphine in 30 ml of anhydrous tetrahydrofuran is added thereafter. The reaction mixture is stirred for 1 h at room temperature, then brought to reflux for 3 h and stirred for a further 20 h at room temperature. The reaction mixture is then treated with water and extracted with chloroform, which is washed with water, dried and evaporated.

The residue obtained is chromatographed on silica gel with a 9:1 chloroform/methanol mixture as eluent, to yield 3.95 g of 7-n-propyl-5-methyl-8-[(2'-cyano-4-biphenylyl)methyl]-1,2,4-triazolo[1,5-c]pyrimidin-2(3H)-one in the form of crystals of melting point 215°-216° C. This compound is identical to that of Example 18.

EXAMPLE 196

7-n-Propyl-5-hydrazino-8-{[2'-(5-tetrazolyl)-4-biphenylyl]methyl}-1,2,4-triazolo[1.5-c]pyrimidin-2(3H)-one Formula (I): $R_1$- n-propyl, $R_2$=NH—$NH_2$, X=NH, Y=CO, X⋯Y=single bond,

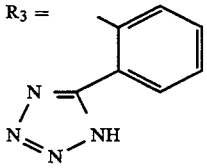

A solution of 14.1 g of 7-n-propyl-5-methylthio-8-{[2'-(5-tetrazolyl)-4-biphenylyl]methyl}-1,2,4-triazolo[4,3-c]pyrimidin-3(2H)-one, prepared in Example 105, and 30 ml of hydrazine hydrate in 100 ml of 2-methoxyethanol is brought to reflux for 3 hours 30 minutes. The reaction mixture is then concentrated under vacuum, treated with water and neutralised by bubbling in sulphur dioxide. The crystals formed are drained, washed with water and dried. 9 g of 7-n-propyl-5-hydrazino-8-{[2'-(5-tetrazolyl)-4-biphenylyl]methyl}-1,2,4-triazolo[1,5c]pyrimidin-2(3H)-one are obtained in the form of crystals of melting point 287°-288° C.

PHARMACOLOGY

I. Principle

The affinity of the products of the examples for angiotensin II receptors is assessed by a technique of displacement of a radiolabelled ligand specifically bound to the adrenal angiotensin II receptors in the rat.

II. Procedure

An aliquot of a rat adrenal homogenate is incubated in the presence of a single concentration of [$^{125}$I]-SIAII(Sar$^1$ Tyr$^4$, Ile$^8$-angiotensin II) which is an angiotensin II receptor antagonist, and two concentrations of competitive agents ($10^5$ M, $10^7$ M) for 60 min at 25° C. The reaction is stopped by adding buffer, followed by rapid filtration through glass-paper filters. The non-specific binding is determined in the presence of angiotensin II.

III. Expression of the results

The results are expressed, for the concentrations tested, as a percentage displacement of the radiolabelled ligand specifically bound to the adrenal angiotensin II receptors.

IV. Results

| Product of example | % displacement of the labelled ligand | |
|---|---|---|
|  | 1E-5M | 1E-7M |
| Example 19 | 66 | 48 |
| Example 20 | 60 | 45 |
| Example 25 | 68 | 54 |
| Example 36 | 65 | 43 |
| Example 42 | 75 | 46 |
| Example 68 | 67 | 33 |
| Example 71 | 73 | 60 |
| Example 74 | 69 | 54 |
| Example 78 | 67 | 52 |
| Example 80 | 74 | 59 |
| Example 90 | 63 | 48 |
| Example 97 | 60 | 38 |
| Example 107 | 71 | 58 |
| Example 109 | 67 | 46 |
| Example 112 | 60 | 41 |
| Example 138 | 61 | 17 |
| Example 146 | 74 | 56 |
| Example 152 | 69 | 57 |

TOXICOLOGY

The products of the examples described exhibit excellent tolerability after oral administration.

Their median lethal dose in the rat was assessed as being greater than 300 mg/kg.

CONCLUSION

The products of the examples described exhibit a good affinity for angiotensin II receptors. On this basis, they may be used beneficially in the various pathologies in which angiotensin II is involved, especially in the treatment of arterial hypertension, cardiac insufficiency and diseases of the arterial wall, at dosages of 1 to 400 mg taken orally and 0.01 to 50 mg administered intravenously, in one or several doses per day.

We claim:

1. Triazolopyrimidine compounds of formula (I):

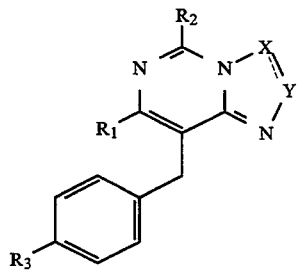

Formula (I)

in which:

$R_1$ represents a lower alkyl radical having 1 to 6 carbon atoms or a $C_3$-$C_7$ cycloalkyl radical, $R_2$ represents a hydrogen atom, a lower alkyl radical having 1 to 6 carbon atoms, a lower haloalkyl radical having 1 to 6 carbon atoms, a group $NR_4R'_4$, an NH—NH$_2$ group or a group $(CH_2)_mOR_4$ or $(CH_2)_mSR_4$, $R_4$ and $R'_4$, which may be identical or different, represent a hydrogen atom or a lower alkyl radical having 1 to 6 carbon atoms and m represents an integer from 0 to 5, the assembly —X   Y— or —Y···X— represents one of the following bivalent radicals:

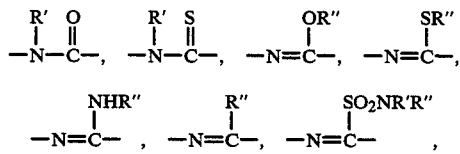

in which R' and R", which may be identical or different, represent:

a hydrogen atom, a lower alkyl radical having 1 to 6 carbon atoms, a lower haloalkyl radical having 1 to 6 carbon atoms or a group $(CH_2)_nCOOR_5,(CH_2)_{n'}$—$OR_5,(CH_2)_{n'}$—O—CO—$R_5$ or $(CH_2)_{n'}SR_5$; n being an integer from 0 to 5, n'being an integer from 1 to 5 and $R_5$ being a hydrogen atom or a lower alkyl radical having 1 to 6 carbon atoms, a phenyl, pyridyl, thienyl or furyl radical, $R_3$ represents an NO$_2$ or NH$_2$ group or represents one of the following radicals:

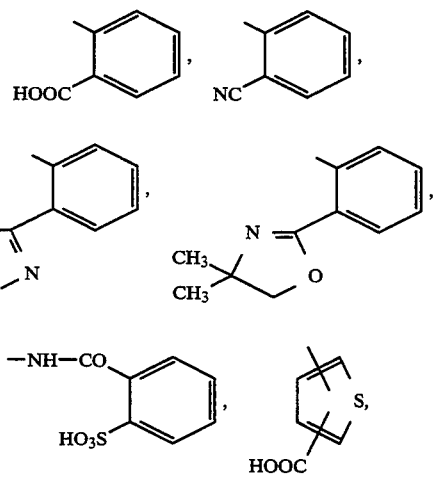

-continued

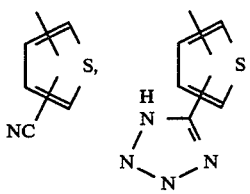

or their tautomeric forms and their addition salts, especially pharmaceutically acceptable addition salts.

2. Triazolopyrimidine compounds according to claim 1, wherein:

$R_1$ represents a lower alkyl radical having 1 to 6 carbon atoms or a $C_3$-$C_7$ cycloalkyl radical:

$R_2$ represents a hydrogen atom, a lower alkyl radical having 1 to 6 carbon atoms, an NH—NH$_2$ group or a group $(CH_2)_mOR_4$ or $(CH_2)_mSR_4$; $R_4$ representing a hydrogen atom or a lower alkyl radical having 1 to 6 carbon atoms and m representing an integer from 0 to 2;

the assembly —X···Y— representing a radical selected from the following bivalent radicals:

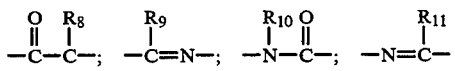

in which:

$R_8$ represents a radical selected from the group consisting of a hydrogen atom, —(CH$_2$)$_n$OH, —(CH$_2$)$_n$COOH, —R$_{12}$, or —(CH$_2$)$_n$COOR$_{12}$; $R_{12}$ representing a lower alkyl radical having 1 to 6 carbon atoms and n an integer equal to 1 or 2;

$R_9$ represents a hydrogen atom or an —SH radical;

$R_{10}$ represents a hydrogen atom or a lower alkyl radical having 1 to 6 carbon atoms;

$R_{11}$ represents a radical selected from the group consisting of a hydrogen atom, a lower alkyl radical having 1 to 6 carbon atoms, a lower haloalkyl radical having 1 to 6 carbon atoms, a phenyl, pyridinyl, —O(CH$_2$)$_n$OH, —OR$_{12}$, —O(CH$_2$)$_n$OCOR$_{12}$, SH, —SR$_{12}$, —S(CH$_2$)$_n$COOR$_{12}$, —S(CH$_2$)$_n$OCOR$_{12}$, —NH(CH$_2$)$_n$COOR$_{12}$, —NR$_{13}$R$_{14}$, SO$_2$NR$_{13}$R$_{14}$, (CH$_2$)$_n$OH, (CH$_2$)$_n$OR$_{12}$, COOH, COOR$_{12}$, (CH$_2$)$_n$COOH, or (CH$_2$)$_n$COOR$_{12}$; n and R$_{12}$ being defined as stated above, R$_{13}$ and R$_{14}$, which may be identical or different, representing a hydrogen atom or a lower alkyl radical having from 1 to 6 carbon atoms;

$R_3$ represents one of the following radicals:

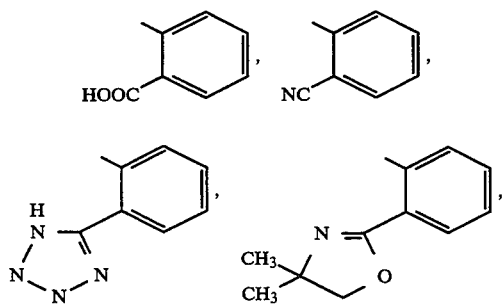

-continued

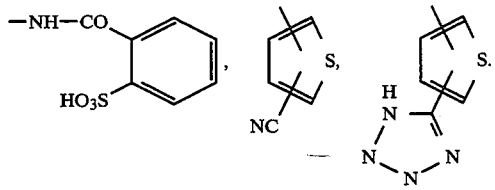

3. Compounds according to claim 2, wherein $R_1$ is a group selected from ethyl, n-propyl and n-butyl.

4. Compounds according to claim 3, wherein $R_2$ is a group selected from methyl, ethyl or methoxymethyl.

5. Compounds according to claim 2, wherein the assembly —X···Y— represents one of the following divalent radicals

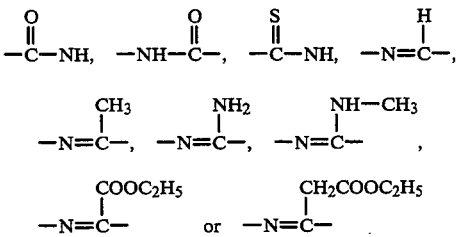

6. Compounds according to claim 4, wherein $R_3$ is a 2-(5-tetrazolyl)phenyl group.

7. Compound according to claim 2, characterised in that it is the following:

7-n-Propyl-5-methyl-8-{[2 - (5-tetrazolyl ) -4-biphenylyl]methyl }- 1,2,4 -triazolo [1,5-c ]pyrimidin-2 (3H) one.

8. Compounds according to claim 1 or 2, characterised in that they are selected from the following:

7-n-Propyl-5-methyl-8-{[2'-(5-tetrazolyl)-4-biphenylyl]methyl]-1,2,4-triazolo[4,3-c]pyrimidin-3(2H)-one;

7-n-Propyl-5-methyl-3-mercapto-8-{[2'-(5-tetrazolyl)-4-biphenyl]methyl}-1,2,4-triazolo[4,3-c]pyrimidine;

7-n-Propyl-2,5-dimethyl-8-{[2'-(5-tetrazolyl)4-biphenylyl]methyl}-1,2,4-triazolo[1,5-c]pyrimidine;

7-n-Propyl-5-methyl-8-{[2'-(5-tetrazolyl)-4-biphenylyl]methyl}-1,2,4-triazolo[1,5-c]pyrimidine;

7-n-Propyl-5-methyl-2-amino-8-{[2'-(5-tetrazolyl)-4-biphenylyl]methyl}-1,2,4-triazolo[1,5-c]pyrimidine;

7-n-Propyl-5-methyl-2-methylamino-8-{[2'-(5-tetrazolyl)-4-biphenylyl]methyl}-1,2,4-triazolo[1,5-c]pyrimidine;

Ethyl 7-n-Propyl-5-methyl-8-{[2'-(5-tetrazolyl)-4-biphenylyl]methyl}-1,2,4-triazolo[1,5-c]pyrimidine-2-carboxylate;

Ethyl [7-n-Propyl-5-methyl-8-{[2'-(5-tetrazolyl)-4-biphenylyl]methyl}-1,2,4-triazolo[1,5-c]pyrimidine-2-yl]acetate;

7-Ethyl-2,5-dimethyl-8-{[2'-(5-tetrazolyl)-4-biphenylyl]methyl}-1,2,4-triazolo[1,5-c]pyrimidine;

7-n-Butyl-5-methyl-8-{[2'-(5-tetrazolyl)-4-biphenylyl]methyl}-1,2,4-triazolo[1,5-c]pyrimidin-2(3H)-one;

7-n-Propyl-5-ethyl-8-{[2'-(5-tetrazolyl)-4-biphenylyl]methyl}-1,2,4-triazolo[1,5-c]pyrimidin-2(3H)-one;

7-n-Propyl-5-methoxymethyl-8-{[2'-(5-tetrazolyl)-4-biphenyl]methyl}-1,2,4-triazolo[1,5-c]pyrimidin-2(3H)-one.

9. Pharmaceutical composition, characterised in that it comprises a pharmaceutically effective amount of at least one compound of formula (I) as defined in claim 1, or one of its pharmaceutically acceptable addition salts, incorporated in a pharmaceutically acceptable excipient, vehicle or carrier.

* * * * *